United States Patent
Bissantz et al.

(10) Patent No.: US 9,957,298 B2
(45) Date of Patent: May 1, 2018

(54) PEPTIDES AS OXYTOCIN AGONISTS

(71) Applicant: Hoffmann-La Roche Inc., Little Falls, NJ (US)

(72) Inventors: Caterina Bissantz, Freiburg (DE); Konrad Bleicher, Freiburg (DE); Christophe Grundschober, Rodersdorf (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days. days.

(21) Appl. No.: 15/368,080

(22) Filed: Dec. 2, 2016

(65) Prior Publication Data
US 2017/0081369 A1     Mar. 23, 2017

Related U.S. Application Data

(63) Continuation of application No. PCT/EP2015/062054, filed on Jun. 1, 2015.

(30) Foreign Application Priority Data

Jun. 3, 2014  (EP) .................................. 14170992

(51) Int. Cl.
C07K 7/16   (2006.01)
C07K 7/56   (2006.01)
A61K 38/00  (2006.01)

(52) U.S. Cl.
CPC ............... *C07K 7/56* (2013.01); *A61K 38/00* (2013.01)

(58) Field of Classification Search
None
See application file for complete search history.

(56) References Cited

FOREIGN PATENT DOCUMENTS

| CN | 102656183 | 3/2016 |
|---|---|---|
| JP | 2001-519786 | 10/2001 |
| JP | 2011-516460 | 5/2011 |
| WO | 2009/122285 A1 | 10/2009 |
| WO | 2011/035330 A2 | 3/2011 |
| WO | 2011/038451 A1 | 4/2011 |
| WO | 2014/095773 A1 | 6/2014 |

OTHER PUBLICATIONS

Smith, Replacement of the Disulfide Bond in Oxytocin by an Amide Group, Journal of Medicinal Chemistry, 1978, vol. 21, No. 1.*
Olff (A Psychobiological Rationale for Oxytocin in the Treatment of Posttraumatic Stress Disorder, 2010 CNS Spectr 15:8 ).*
Acheson (The effect of intranasal oxytocin treatment on conditioned fear extinction and recall in a healthy human sample, Psychopharmacology (2013) 229:199-208).*
Smith, Replacement of the Disulfide Bond in Oxytocin by an Amide Group, Journal of Medicinal Chemistry, 1978, vol. 21, No. 1, of record (Year: 1978).*
Belec et al., "A study of the relationship between biological activity and prolyl amide isomer geometry in oxytocin using 5-tert-butylproline to augment the Cys(6)-Pro(7) amide cis-isomer population" J Med Chem 43:1448-55 ( 2000).
Clark W. Smith et al., "Replacement of the Disulfide Bond in Oxytocin by an Amide Group. Synthesis and Some Biological Properties of [cyclo-(1-L-Aspartic acid,6-L.alpha.,beta.-diamonipropionicacid)] oxytocin." Journal of Medicinal Chemistry 21(1):117-120 (Jan. 1, 1978).
Hase et al., "Effect of an Amide Group in Place of the Disulfide Bridge in Deamino-oxytocin" Journal of medicinal chemistry 15(10):1017-1019 (Oct. 1972).
IPRP for PCT/EP2015/062054.
IPRP for PCT/EP2015/062314.
Jake L. Stymiest et al., "Synthesis of Biologically Active Dicarba Analogues of the Peptide Hormone Oxytocin Using Ring-Closing Metathesis" Organic Letters, American Chemical Society, US 5(1):47-49 (Jan. 1, 2003).
Jake L. Stymiest et al., "Synthesis of Oxytocin Analogueswith Replacement of Sulfur by Carbon Gives Potent Antagonists with Increased Stability" The Journal of Organic Chemistry 70(20):7799-7809 (Sep. 30, 2005).
Jin-Ting, Liu et al., Advances in Psychological Science 19(10):1480-1492 ( 2011).
PCT ISR for PCT/EP2013/076783.
Qi, Jia, Health and Medical Sciences E079-40.
Roderich Walter et al., "A Neurohypophyseal Hormone Analog with Selective Oxytocin-Like Activities and Resistance-to Enzymatic Inactivation: An Approach to the Design of Peptide Drugs*" Proc. Nat. Acad. Sci. (www.pnas.org/content/71/5/1901.full.pdf), 71(5):1901-1905 (May 1, 1974).
Wisniewski Kazimierz et al., "New, Potent, and Selective Peptidic Oxytocin Receptor Agonists" Journal of Medicinal Chemistry 57(12):5306-5317 (May 29, 2014).
Written Opinion for PCT/EP2015/067881.
Bodanszky M. et al., "Synthesis and Some Pharmacological Properties of 8-L-Methionine-oxytocin" Journal of Medicinal Chemistry 22(3):270-273 ( 1979).
Bodanszky M. et al., "Synthesis and Some Pharmacological Properties of 8-L-Tryptophan oxytocin" Journal of Medicinal Chemistry 23(11):1258-1261 ( 1980).
Czernichow P. et al., "Immunochemical Analysis of Rabbit Antibodies against Ocytocin" Immunochemistry 13(5):389-394 ( 1976).
Roderich Walter, "Partial Purification and Characterization of Post-Proline Cleaving Enzyme" Biochimica et Biophysica Acta 422:138-158 ( 1976).

* cited by examiner

*Primary Examiner* — Lianko G Garyu
*Assistant Examiner* — Khalid Kader
(74) *Attorney, Agent, or Firm* — Tamara A. Kale

(57) ABSTRACT

The present compounds compounds are oxytocin receptor agonists for the treatment of autism, stress, including post traumatic stress disorder, anxiety, including anxiety disorders and depression, schizophrenia, psychiatric disorders and memory loss, alcohol withdrawal, drug addiction and for the treatment of Prader-Willi Syndrome.

8 Claims, No Drawings

PEPTIDES AS OXYTOCIN AGONISTS

CROSS REFERENCE TO RELATED APPLICATIONS

This application is a continuation of International Application No. PCT/EP2015/062054, having an international filing date of 1 Jun. 2015, the entire contents of which are incorporated herein by reference, and which claims benefit under 35 U.S.C. 119 to European Patent Application No. 14170992.3, filed 3 Jun. 2014, the entire contents of which are incorporated herein by reference.

The invention relates to compounds of formula

I

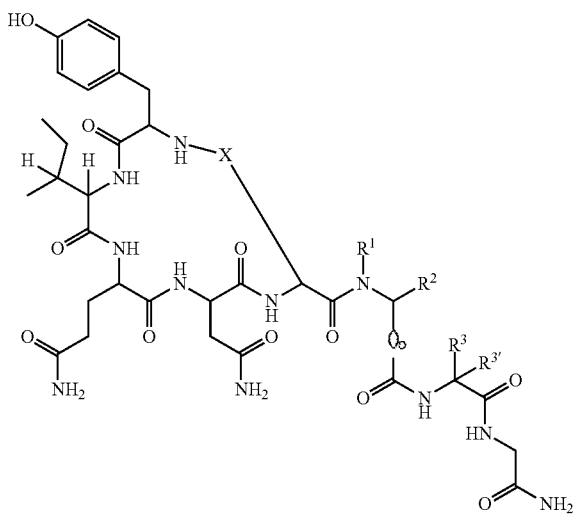

wherein
$R^1$ is hydrogen, lower alkyl or cycloalkyl;
$R^2$ is hydrogen or
$R^1$ and $R^2$ may form together with the N and C atom to which they are attached a pyrrolidine ring optionally substituted by one or two F-atoms or by hydroxy, or may form an azetidine or a piperazine ring;
$R^3$ is hydrogen, lower alkyl, lower alkyl substituted by hydroxy, —$(CH_2)_2C(O)NH_2$, benzyl, phenyl, —$CH_2$-five membered aromatic heterocyclic group, $CH_2$-indolyl, —$CH_2$-cycloalkyl, cycloalkyl or —$(CH_2)_2$—S-lower alkyl;
$R^{3'}$ is hydrogen or lower alkyl; or
X is —C(O)—$CHR^4$—$CHR^{4'}$—C(O)—NH—$CH_2$—
$R^4/R^{4'}$ are hydrogen or one of $R^4$ or $R^{4'}$ is amino:
o is 0 or 1;
or to pharmaceutically acceptable acid addition salt, to a racemic mixture or to its corresponding enantiomer and/or optical isomers thereof.

It has been found that the present compounds are oxytocin receptor agonists, which compounds are oxytocin analogs that retain oxytocin bioactivity. Such analog molecules are capable of acting in a manner similar to endogenous oxytocin, including binding the oxytocin receptor. Analogs of oxytocin have completely new molecular structures.

Oxytocin is a nine amino acid cyclic peptide hormone with two cysteine residues that form a disulfide bridge between position 1 and 6. Human oxytocin comprises the sequence Cys-Tyr-Ile-Gln-Asn-Cys-Pro-Leu-Gly.

Peptides have emerged as a commercially relevant class of drugs that offer the advantage of greater specifity and potency and lower toxicity profiles over traditional small molecule pharmaceuticals. They offer promising treatment options for numerous diseases, such as diabetes, HIV, hepatitis, cancer and others, with physicians and patents becoming more accepting of peptide-based medicines. The present invention relates to peptidic oxytocin receptor agonists, which also include the natural hormone oxytocin and carbetocin.

Oxytocin is a potent uterotonic agent for the control of uterine atony and excessive bleeding, clinically used to induce labour, and has been shown to enhance the onset and maintenance of lactation (Gimpl et al., Physiol. Rev., 81, (2001), 629-683, Ruis et al., BMJ, 283, (1981), 340-342). Carbetocin (1-deamino-1-carba-2-tyrosine (O-methyl)-oxytocin) is also a potent uterotonic agent clinically used for the control of uterine atony and excessive bleeding.

Peptidic oxytocin agonists may be used for the treatment of Prader-Willi Syndrome, which is a rare genetic disorder which affects one child in 25,000.

Further research indicates that oxytocin agonists are useful for the treatment of inflammation and pain, including abdominal and back pain (Yang, Spine, 19, 1994, 867-71), sexual dysfunction in both male (Lidberg et al., Pharmakopsychiat., 10, 1977, 21-25) and female (Anderson-Hunt, et al., BMJ, 309, 1994, 929), irretable bowel syndrome (IBS, Louvel et al., Gut, 39, 1996, 741-47), constipation and gastrointestinal obstruction (Ohlsson et al., Neurogastroenterol. Motil., 17, 2005, 697-704), autism (Hollander et al., Neuropsychopharm., 28, 2008, 193-98), stress, including post traumatic stress disorder (PTSD) (Pitman et al., Psychiatry Research, 48, 107-117), anxiety, including anxiety disorders and depression (Kirsch et al., J. Neurosci., 25, 49, 11489-93, Waldherr et al., PNAS, 104, 2007, 16681-84), surgical blood loss or control of post-partum haemorrhage (Fujimoto et al., Acta Obstet. Gynecol., 85, 2006, 1310 -14), labor induction and maintenance (Flamm et al., Obstet. Gynecol., 70, 1987, 70-12), wound healing and infection, mastitis and placenta delivery, and osteoporosis. Additionally, oxytocin agonists may be useful for the diagnosis of both cancer and placental insufficiency.

Furthermore, the Articles "Intranasal Oxytocin blocks alcohol withdrawal in human subjects" (Alcohol Clin Exp Res, Vol, No. 2012) and "Breaking the loop: Oxytocin as a potential treatment for drug addiction" (Hormones and Behavior, 61, 2012, 331-339) propose to treat alcohol withdrawal and drug addiction with a oxytocin agonist.

Oxytocin and its receptors exists in areas of the brain implicated in the symptoms of schizophrenia, such as the nucleus accumbens and the hippocampus. The oxytocin receptor agonists may be used for the treatment of autism, stress, including post traumatic stress disorder, anxiety, including anxiety disorders and depression, schizophrenia, Alzheimer's disease, psychiatric disorders, memory loss and metabolic diseases (WO2012/016229).

Objects of the present invention are novel compounds of formula I and the use of compounds of formula I and their pharmaceutically acceptable salts for the treatment of CNS diseases related to the oxytocin receptor, which diseases are autism, stress, including post traumatic stress disorder, anxiety, including anxiety disorders and depression, schizophrenia, psychiatric disorders and memory loss, alcohol withdrawal, drug addiction and for the treatment of Prader-Willi Syndrome.

Further objects are the preparation of novel compounds of formula I and medicaments, containing them.

The present invention may provide selective, efficacious compounds, providing alternatives and/or improvements in the treatment of certain CNS diseases including autism, stress, including post traumatic stress disorder, anxiety, including anxiety disorders and depression, schizophrenia, psychiatric disorders and memory loss, alcohol withdrawal, drug addiction and for the treatment of Prader-Willi Syndrome.

It has been shown that the present peptides have a very good selectivity to the vasopressin receptors V1a and V2 as shown in the table. This may have a major advantage for use as medicament to avoid side effects. These physiological effects may be considered to be undesirable side effects in the case of medicines aimed at treating diseases of the central nervous system. Therefore it is desirable to obtain medicines having selectivity for the oxytocin receptor vs vasopressin receptor.

As used herein, the term "lower alkyl" denotes a saturated straight- or branched chain group containing from 1 to 7 carbon atoms, for example, methyl, ethyl, propyl, isopropyl, n-butyl, i-butyl, 2-butyl, t-butyl and the like.

The term "lower alkyl substituted by hydroxy" denotes a lower alkyl group as defined above, wherein at least one hydrogen atom is replaced by a hydroxy group.

The term "cycloalkyl" denotes a cyclic alkyl chain, containing from 3 to 6 carbon atoms.

As used herein, the term "five-membered aromatic heterocyclic group" denotes an imidazolyl, thiophenyl, furanyl, pyrrolyl, pyrazolyl, oxazolyl, oxadiazolyl or isoxazolyl group.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The preferred five-membered heterocyclic ring is an imidazole ring.

Preferred are compounds of formula I, wherein o is 0.

A further embodiment are compounds of formula I, wherein $R^1$ is methyl or cyclopropyl.

A furher embodiment are compounds of formula I, wherein $R^1$ and $R^2$ may form together with the N and C atom to which they are attached a pyrrolidine ring.

The following specific compounds have been prepared and tested for their agonistic activity on the oxytocin receptor:

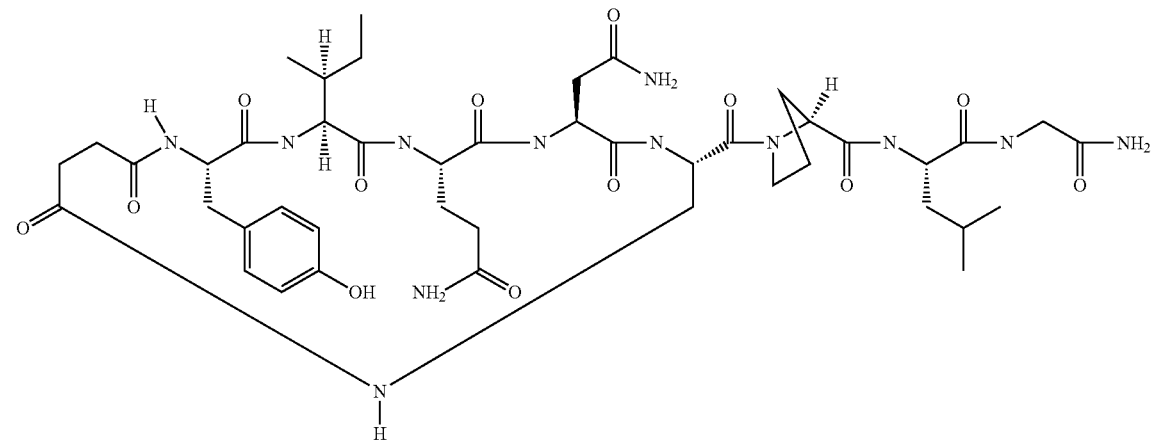

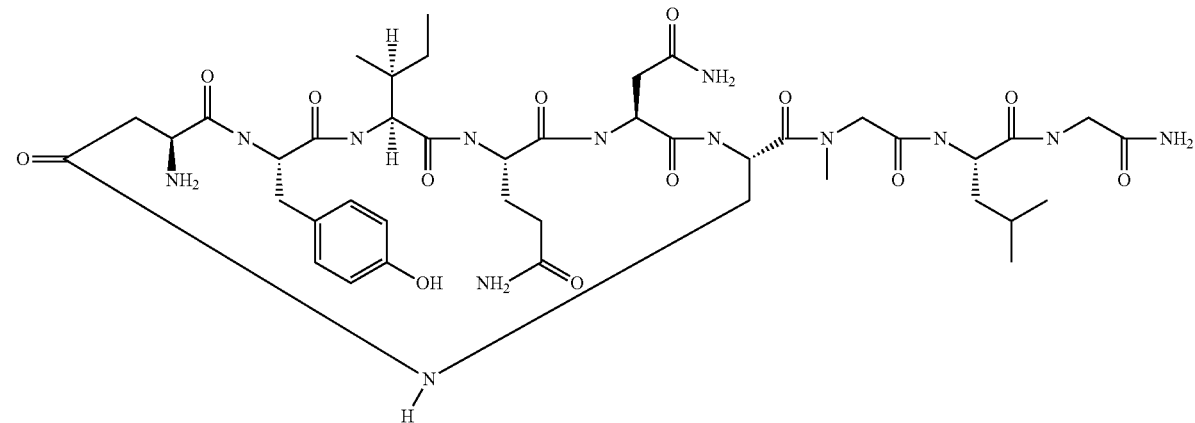

-continued
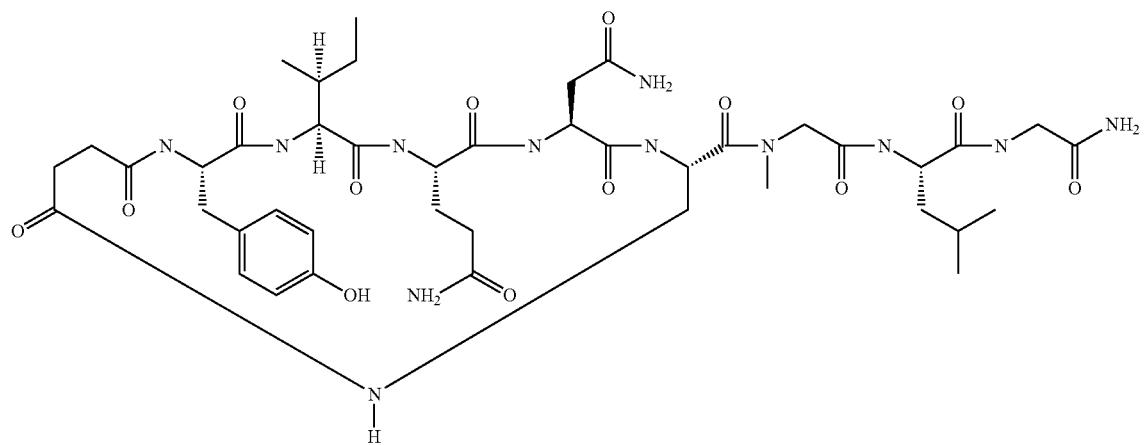
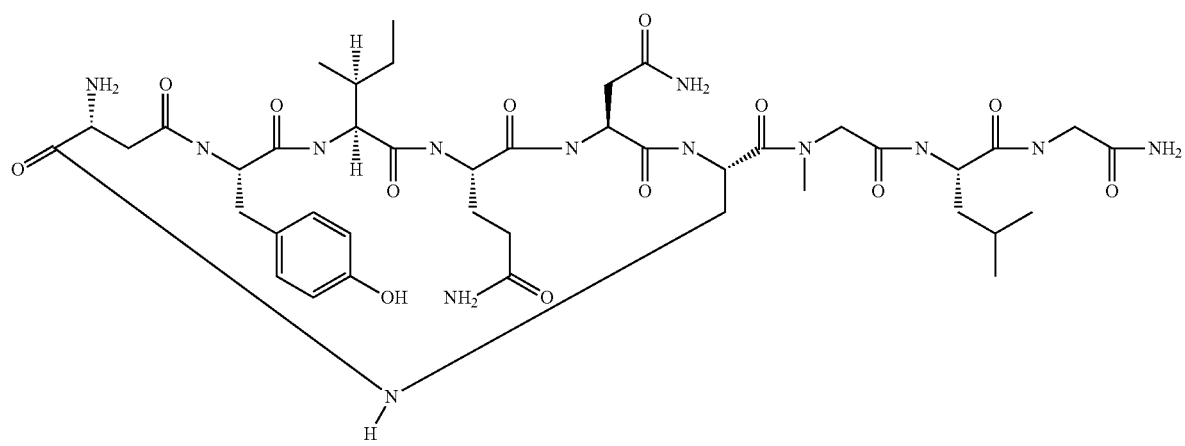
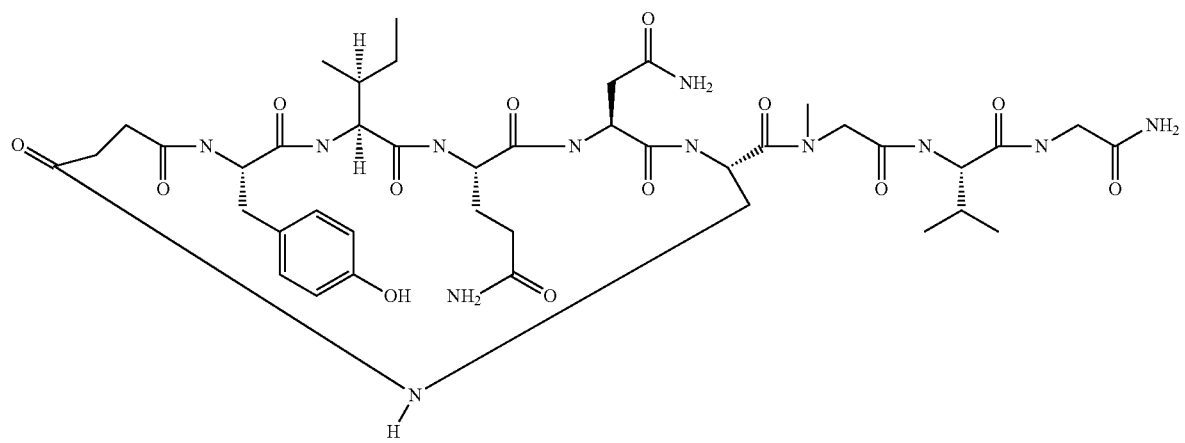

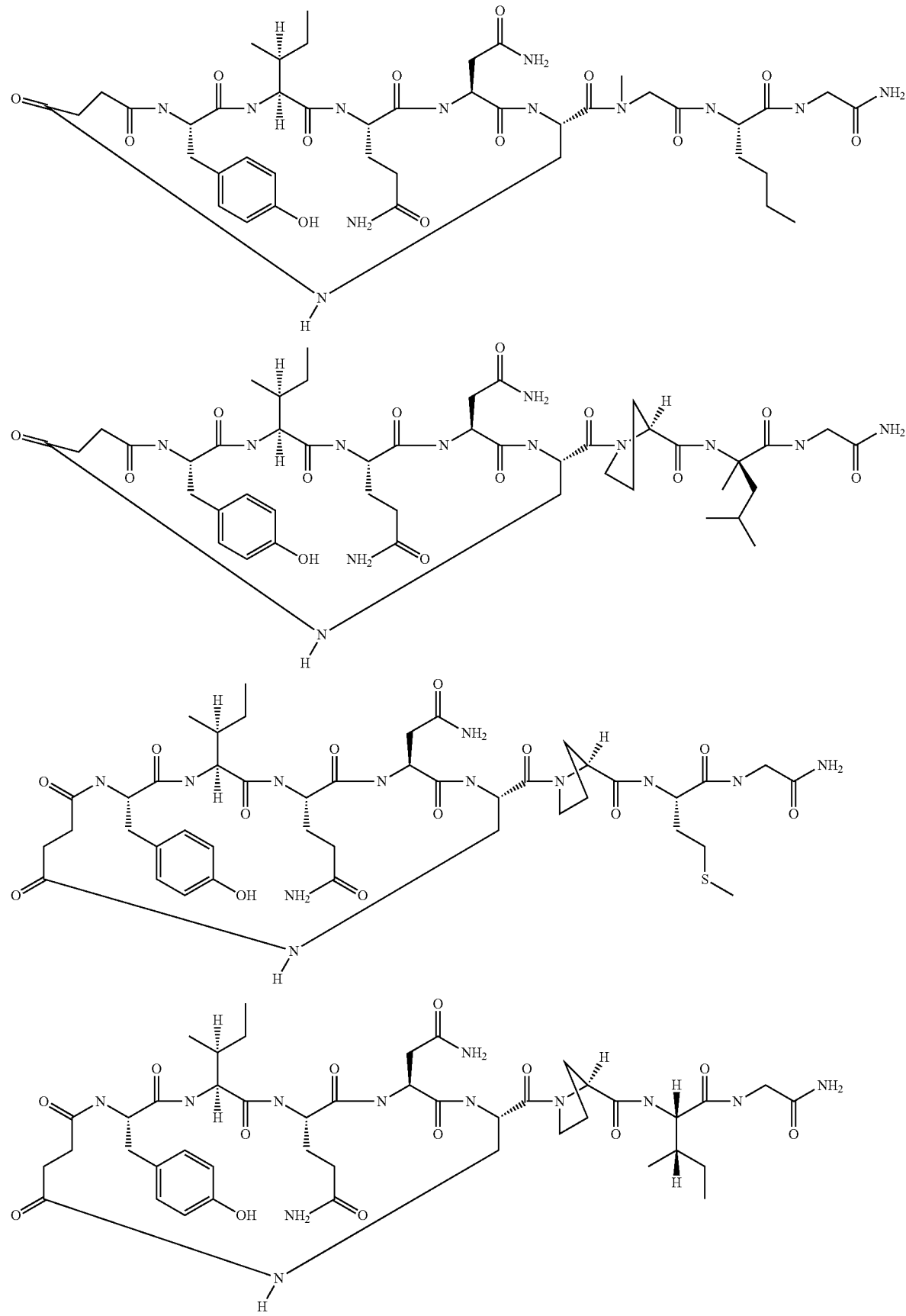

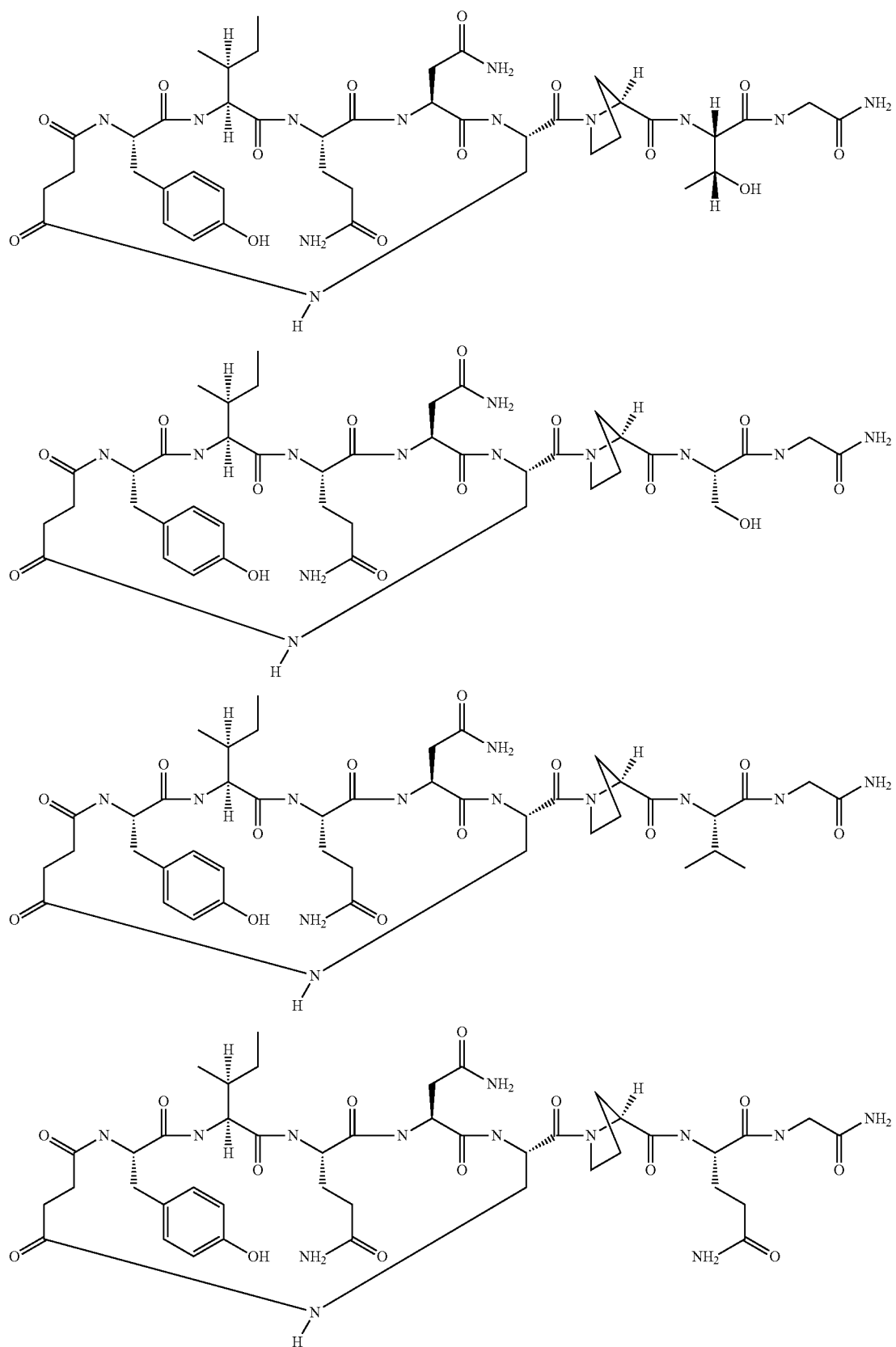

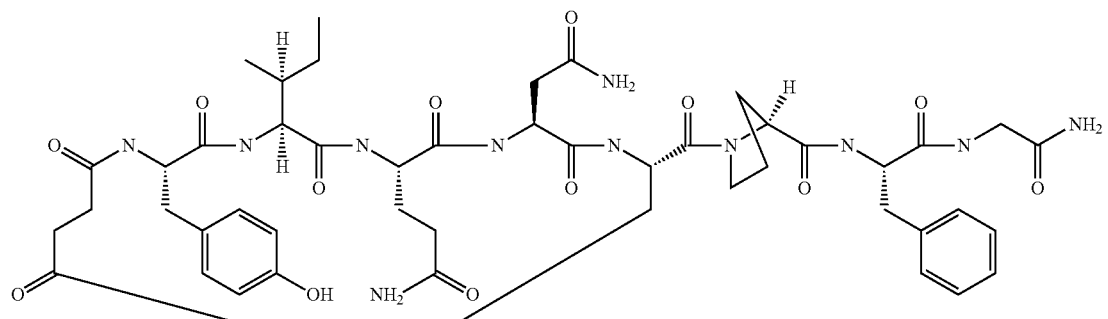
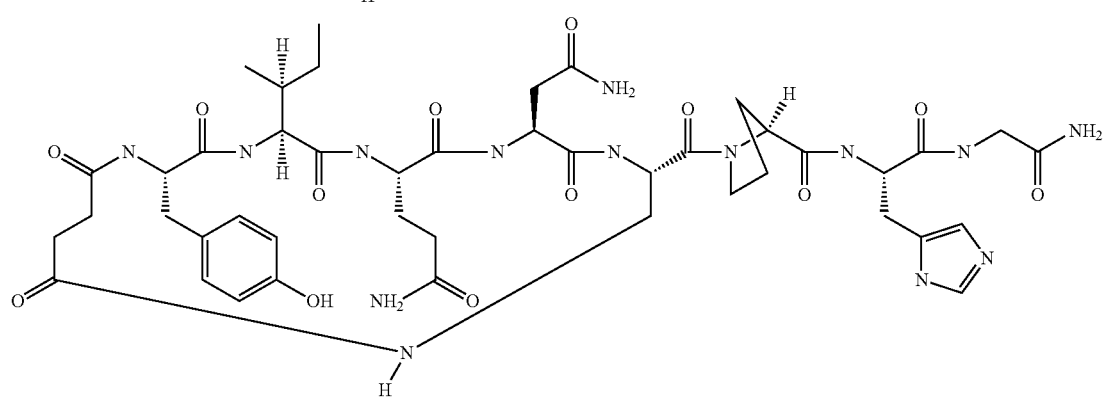
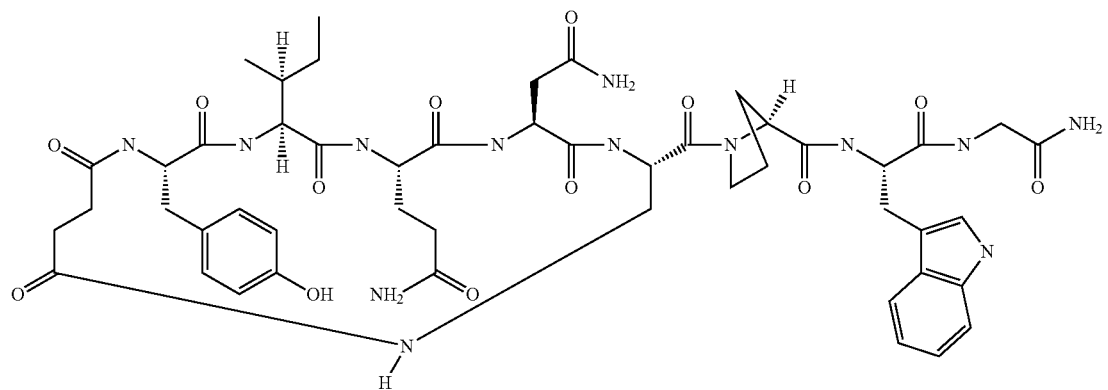
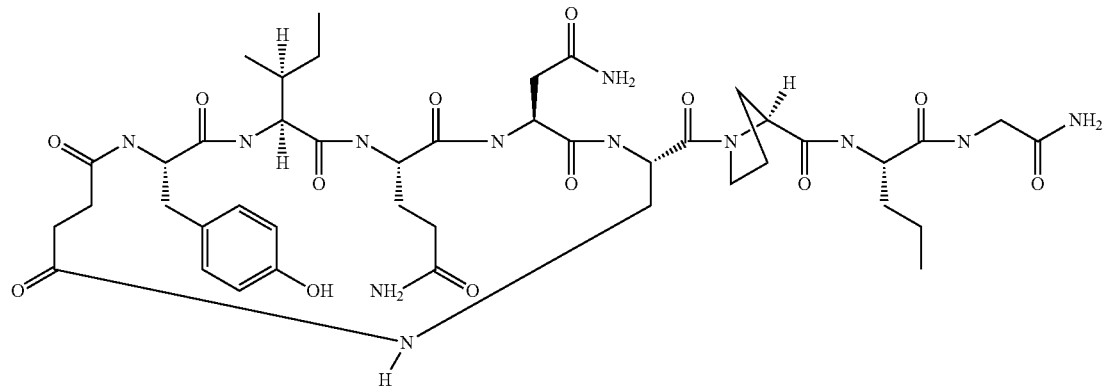

-continued
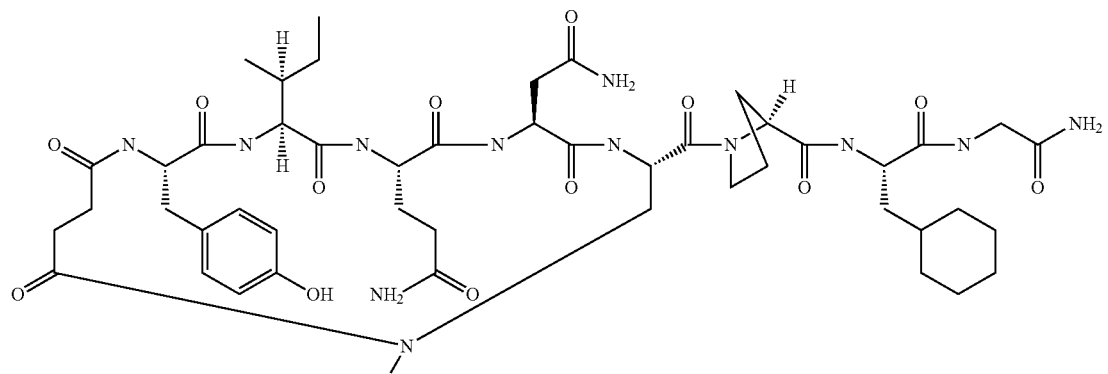
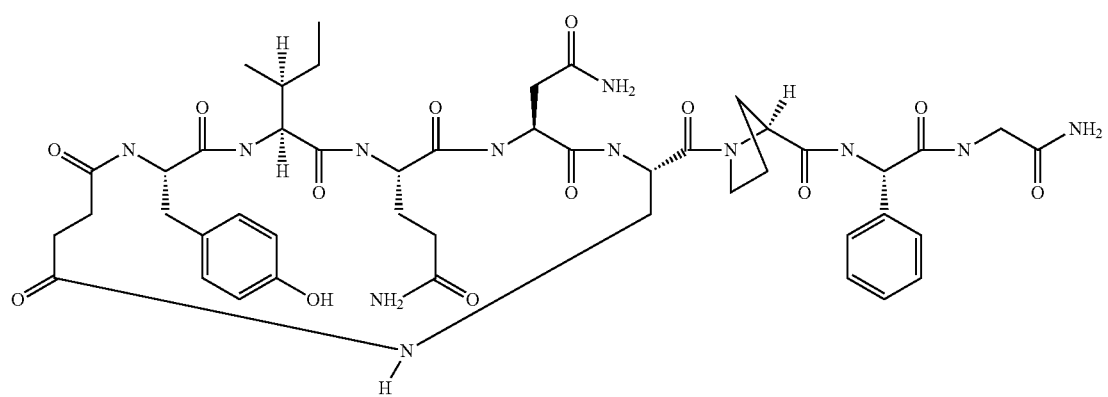
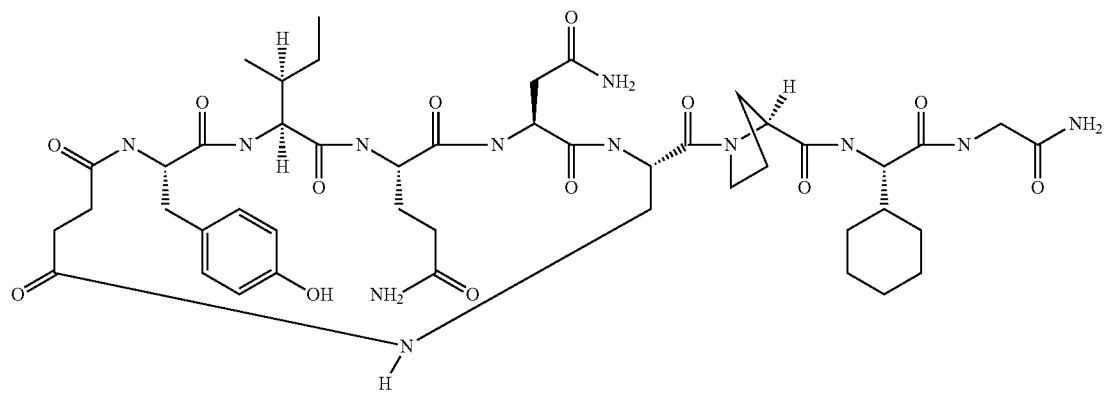
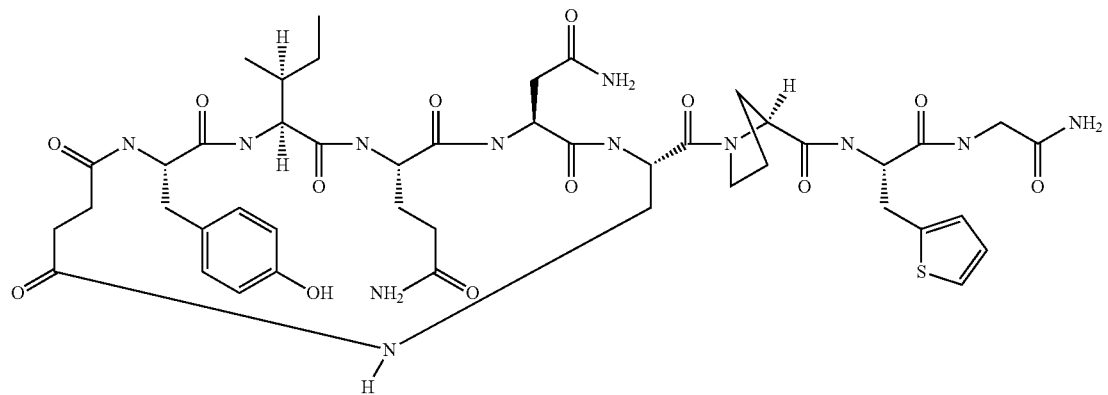

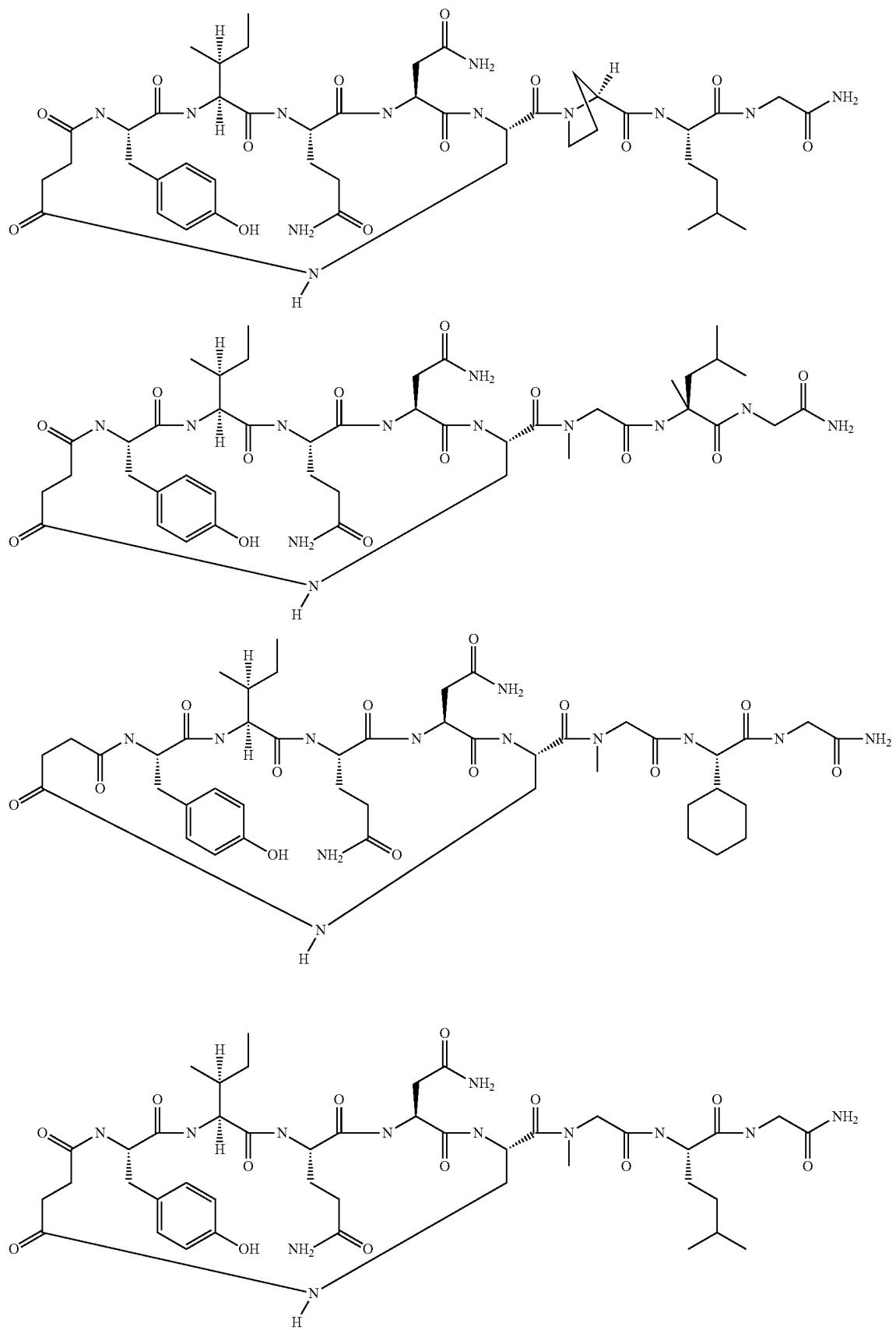

-continued
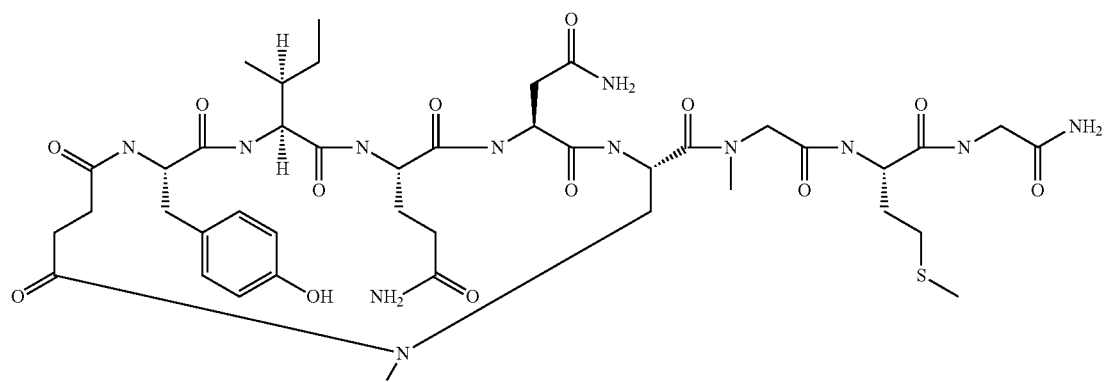
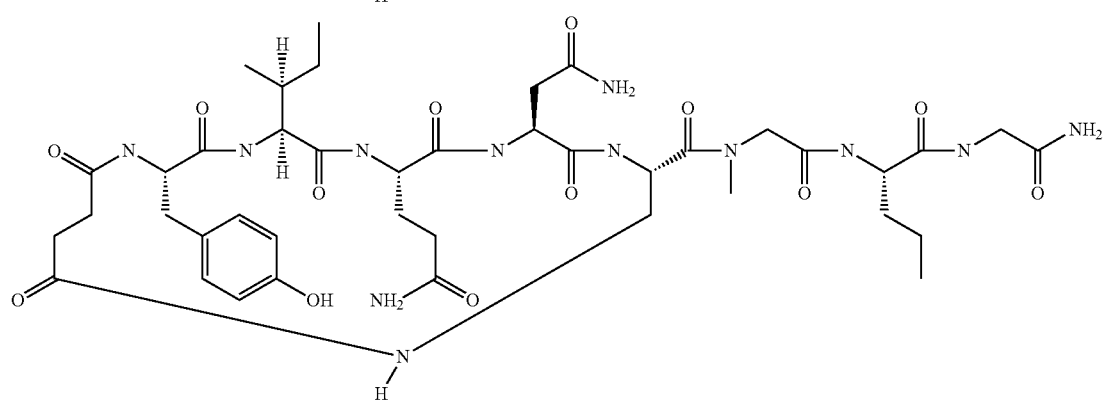
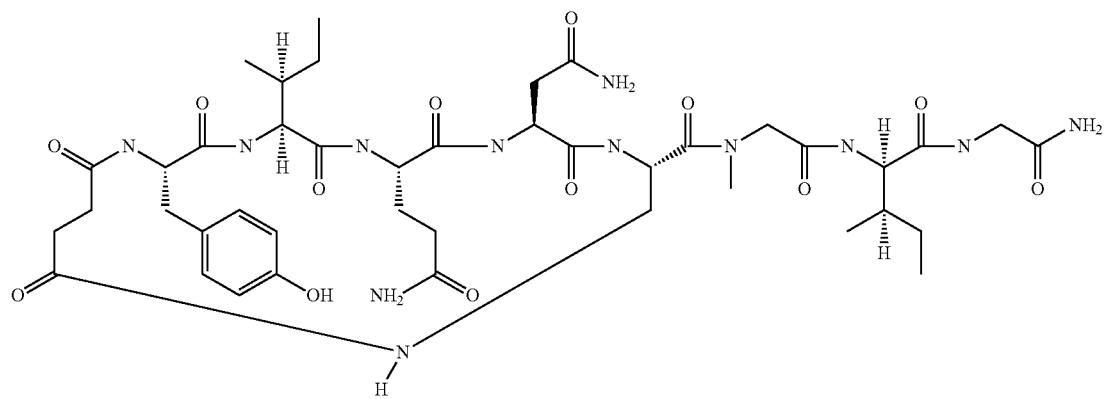
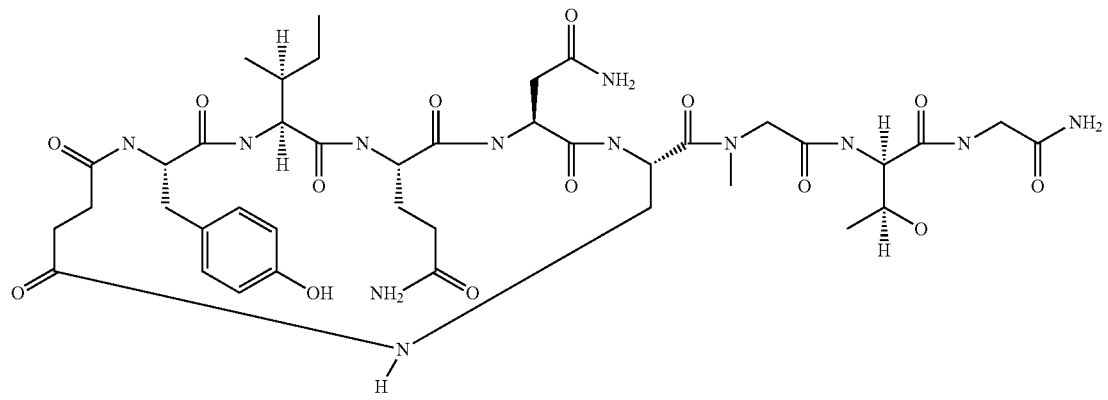

-continued
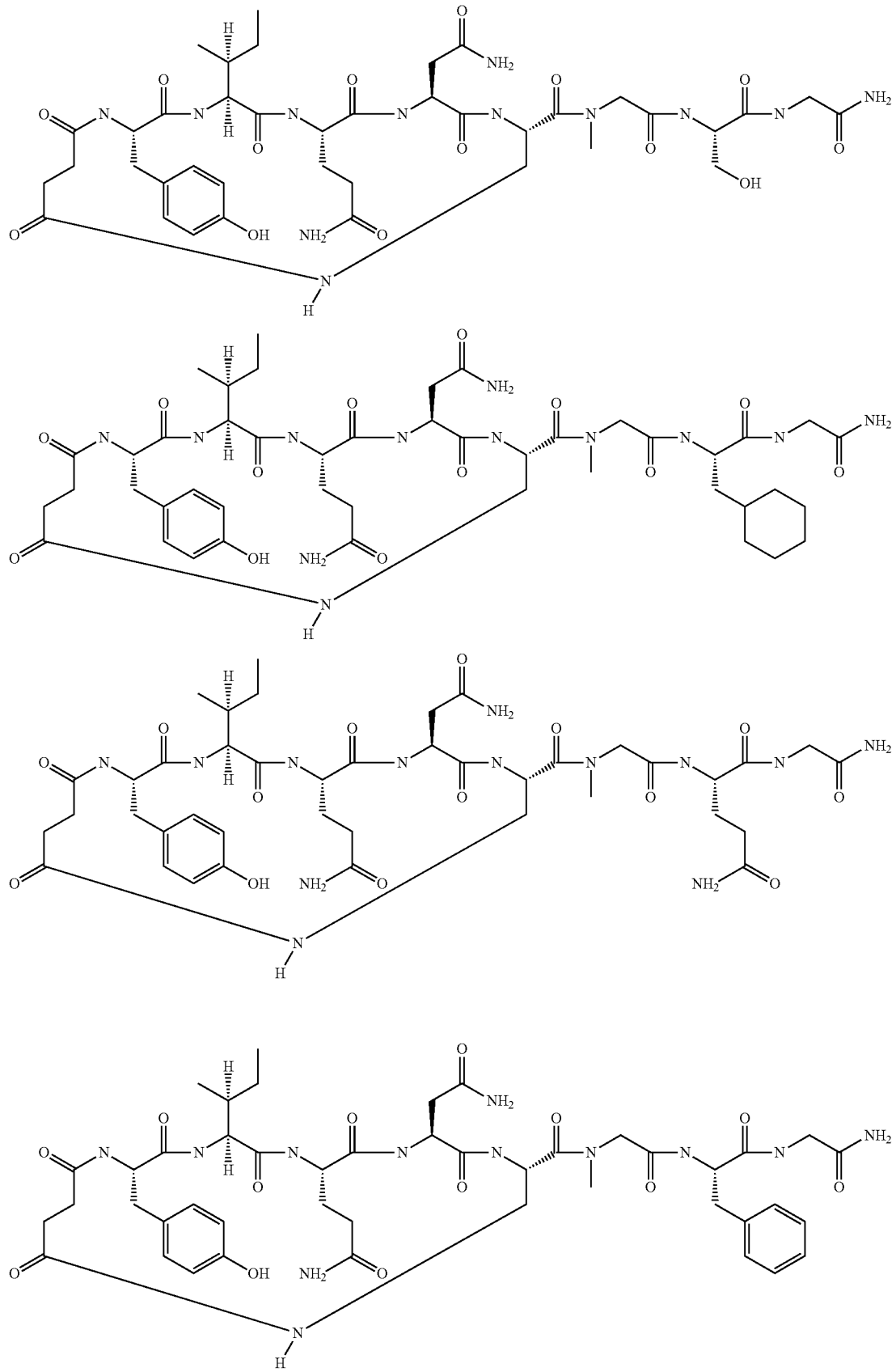

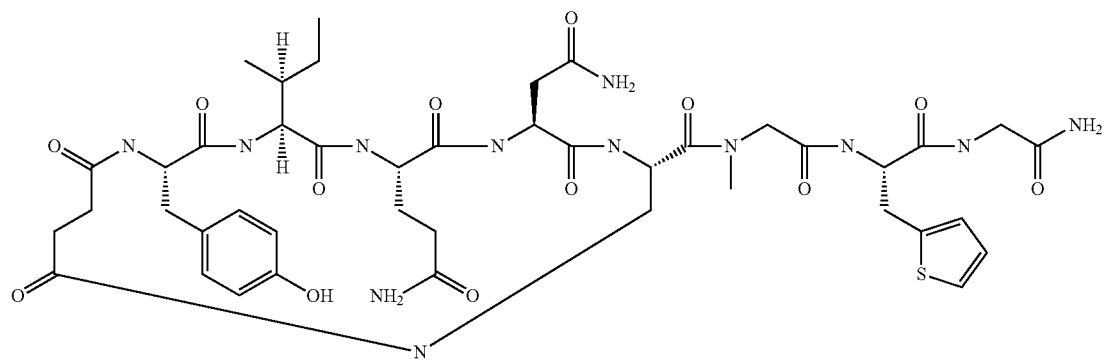
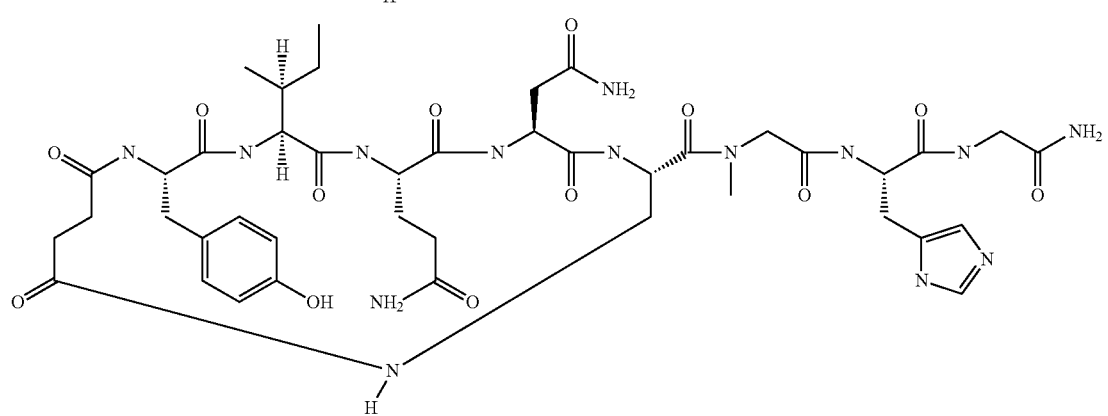
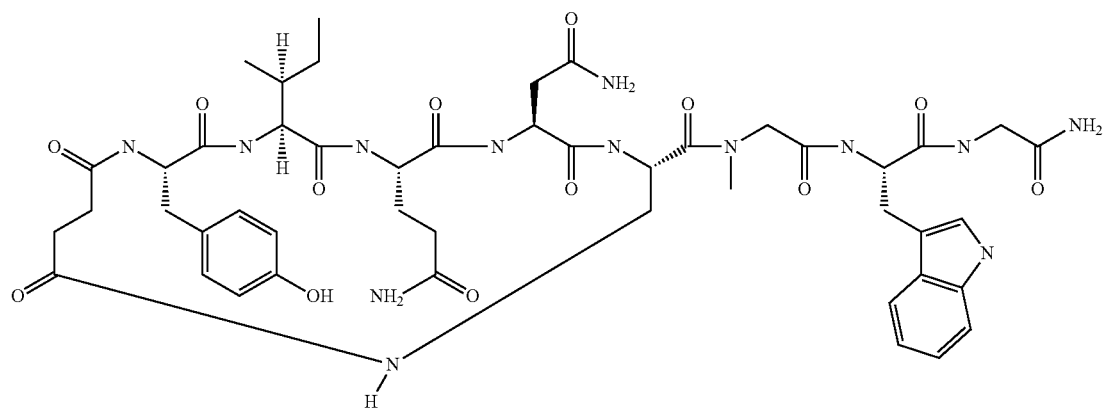
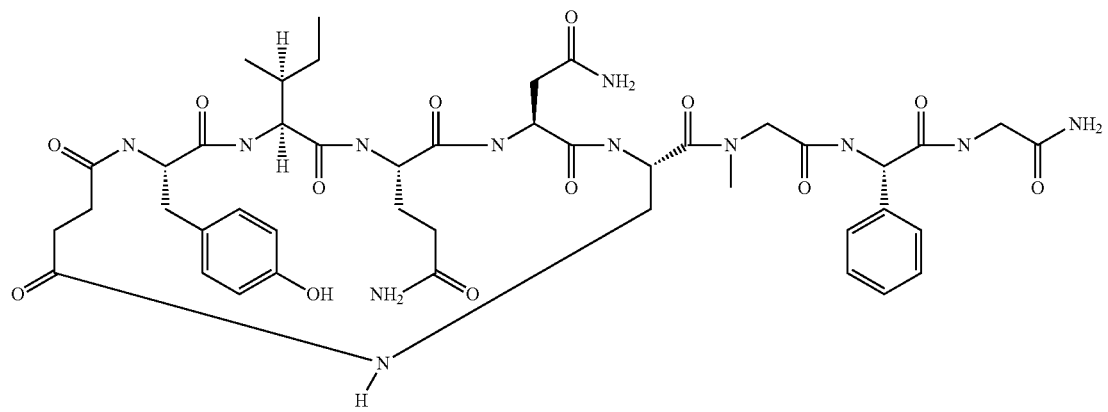

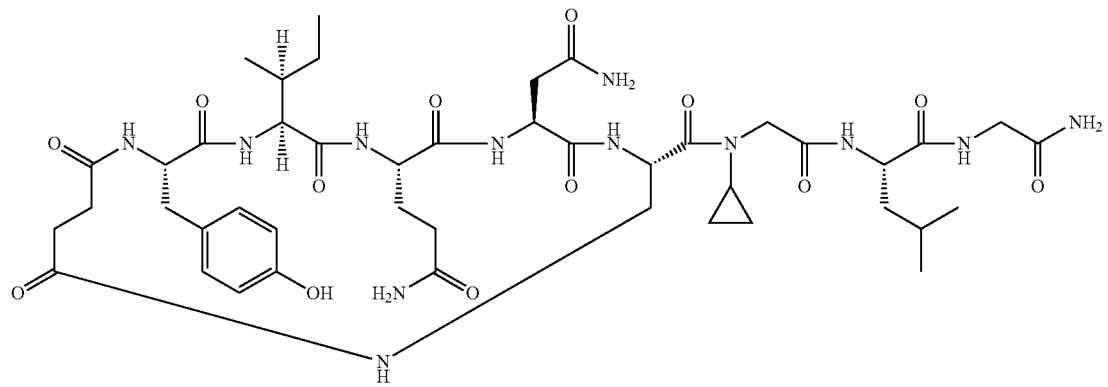
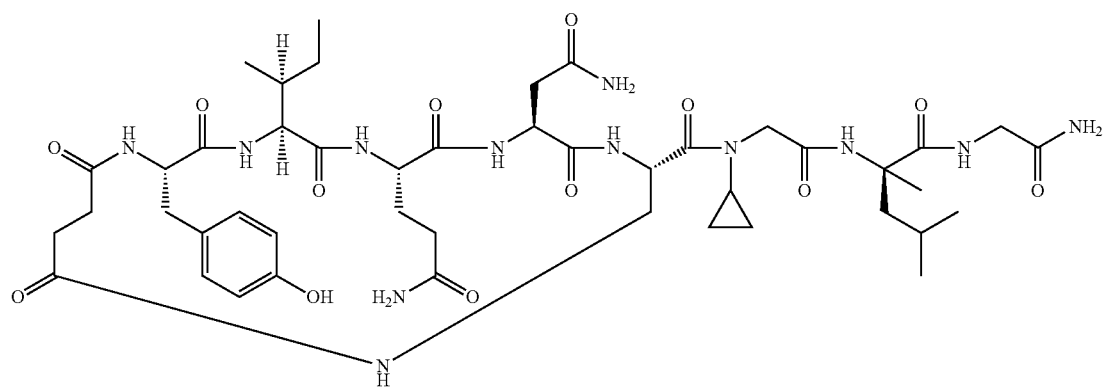
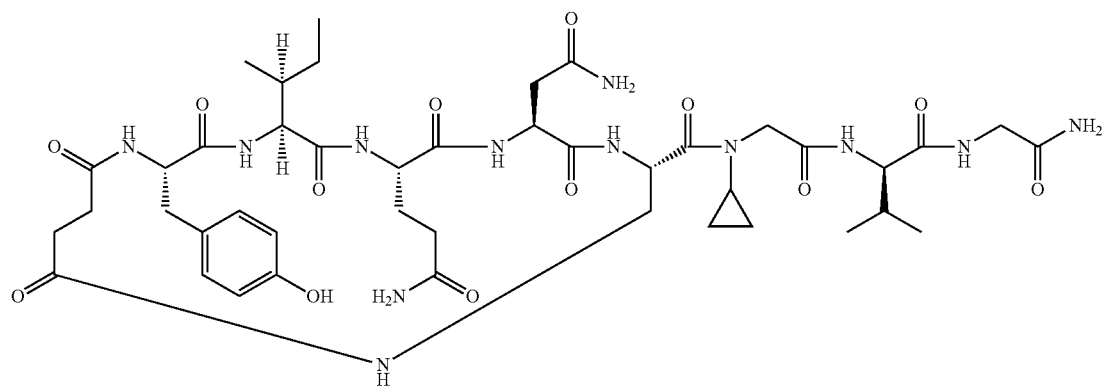
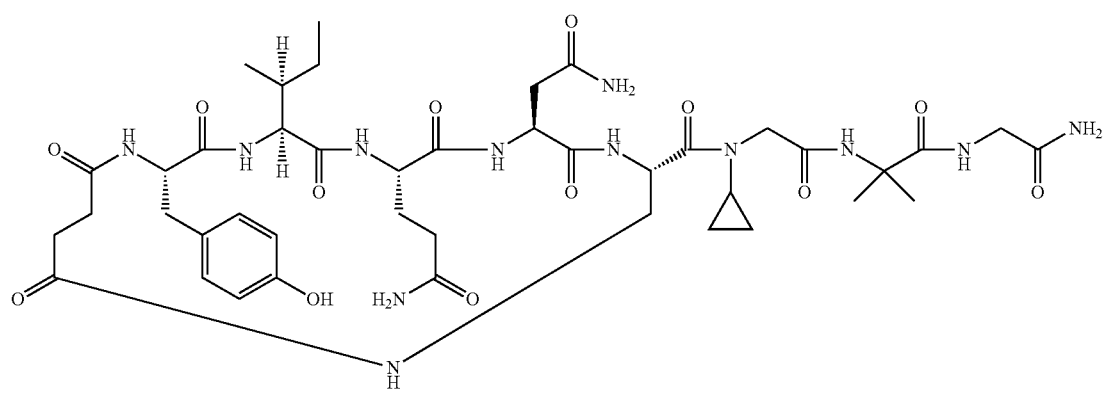

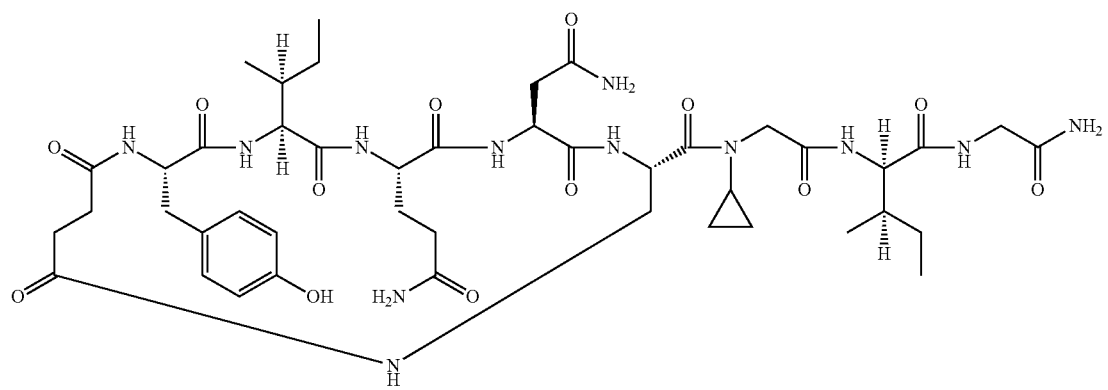
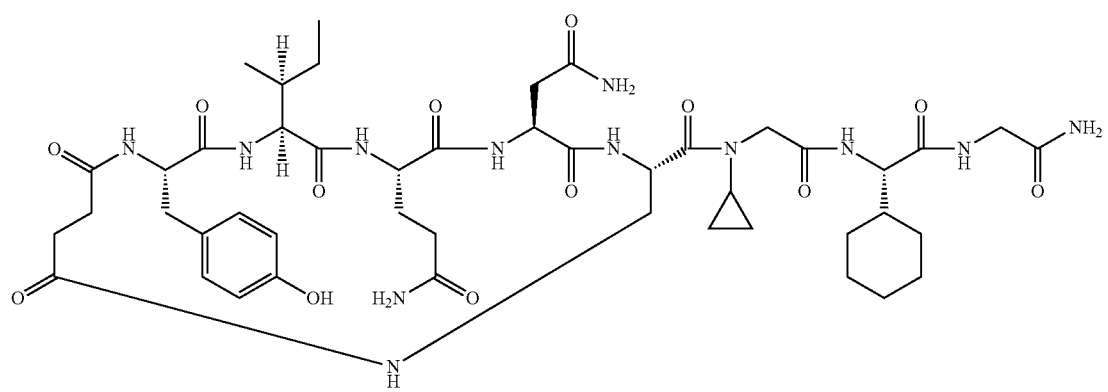
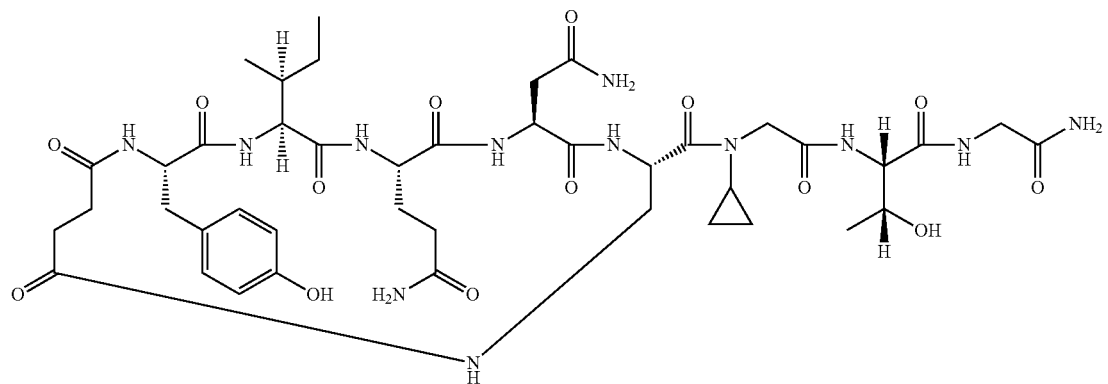
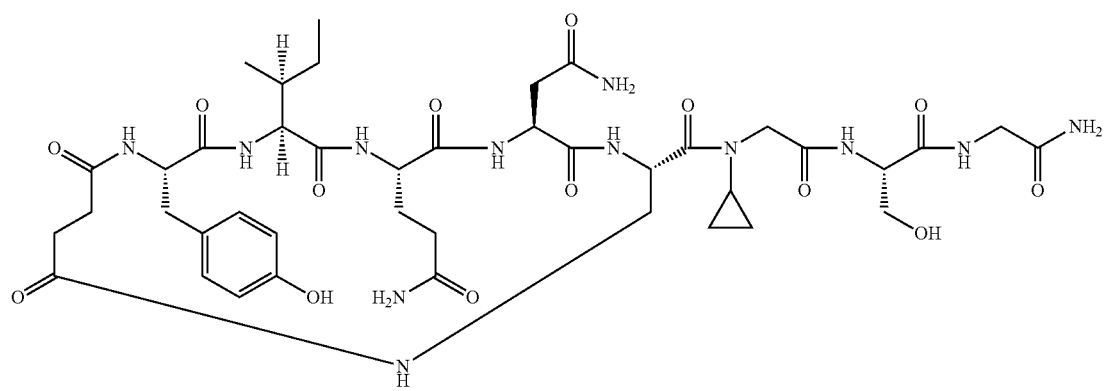 [SMILES: CC[C@H](C)[C@@H]1NC(=O)[C@H](Cc2ccc(O)cc2)NC(=O)CCC(=O)NC[C@@H](C(=O)N(CC(=O)N[C@@H](CO)C(=O)NCC(N)=O)C2CC2)NC(=O)[C@H](CC(N)=O)NC(=O)[C@H](CCC(N)=O)NC1=O]

The compounds herein were synthesized by standard methods in solid phase peptide chemistry utilizing both Fmoc and Boc methodology. Reactions carried out manually were performed at room temperature, while microwave assisted peptide synthesis was performed at elevated temperature.

General Synthesis Description:

The cyclic peptides can be generated either via on-bead cyclisation (Allyl/Aloc strategy METHOD A) or as fully deprotected linear peptides via solution phase cyclisation (METHOD B).

Linear peptides were either synthesized manually or using microwave technology via state-of-the-art solid phase synthesis protocols (Fmoc-chemistry) as referenced by e.g.: Kates and Albericio, Eds., "Solid Phase Synthesis: A practical guide", Marcel Decker, New York, Basel, 2000. As a solid support TentaGel-S-RAM resin (0.24 meq/g) was used. All Fmoc-amino acids were added in a 4-fold excess after activation with HOBT/HBTU 1:1 (0.5 mol/L in DMF) and 4 eq of DIPEA (2 mol/L in NMP). Fmoc-cleavage was achieved with 20% Piperidine in DMF.

Allyl/Aloc-Cleavage & Lactam-Cyclisation:

METHOD A: The resin-linked peptides were treated manually with a solution of 20 eq phenylsilane in DCM and 0.05 eq of tetrakis triphenylphosphine palladium for 30 min at RT. This procedure was repeated. The resin was washed with a solution of 0.5% sodium dithiocarbamate in DMF. For the on-bead lactam formation, again activation reagent was added to the resin and shaken for additional 8 h at RT. Completion of cyclisation was verified via Ninhydrin-test.

METHOD B: Peptides were cyclized in solution after deprotection and cleavage from the resin and standard work-up. Crude peptides were treated with standard peptide activation regents in DMF. The cyclisation was monitored via HPLC.

Cleavage & Work-up:

A cleavage-cocktail of trifluoroacetic acid, triisopropylsilane and water (95/2.5/2.5) was added to the resin and shaken for 1 h at RT. Cleaved peptides were precipitated in cold Ether (−18° C.). The peptides were centrifuged and the residue washed twice with cold ether. The residues were again dissolved in water/acetonitrile and lyophilized.

Purification:

Peptides were purified using reversed phase high performance liquid chromatography (RP-HPLC) using a Reprospher 100 C18-T Column (100×4.6 mm, 5 u particle size) as a stationary phase and water/acetonitrile as eluent (Gradient 1-50% MeCN over 30 min). Fractions were collected and analyzed by LC/MS. Pure product samples were combined and lyophilized. All peptides were obtained as white powders with a purity >85%. Product identification was obtained via mass spectrometry.

All standard amino acids were purchased from CEM. Fmoc-SAR-OH and Fmoc-N-Cyclopropyl-Glycine were purchased from Bachem and Enamine respectively. Mono-tBu-Succinate were purchased from Sigma-Aldrich Synthesis of Mono-allyl Succinate:

A solution of 46 mmol of 4-tert-butoxy-4-oxobutanoic acid (Sigma-Aldrich) in 70 ml THF and 92 mmol DIPEA was cooled 0° C. Now a solution of 55 mmol of 3-iodoprop-1-ene (Fluka) in 6 ml of THF was added dropwise and warmed up to RT and stirred overnight. The reaction mixture was extracted with aqueous bicarbonate, dried over sodium sulfate and the solvent evaporated. 3.7 g of brown oil was obtained. Crude material was purified via Kieselgel chromatography to yield 3.4 g of di-ester. The intermediate was dissolved in 10 ml DCM and 5 ml of TFA added at RT and stirred overnight. Solvent and TFA were evaporated to yield 1.6 g of final product.

The detailed description for the synthesis of example 1 is provided to further illustrate the synthesis conditions:

Peptide Synthesis:

The peptide was synthesized using CEM Microwave technology with coupling times of 5 minutes per amino acid at elevated temperature (78° C.) and a 0.25 mmol scale. The synthesis is carried out using the TentalGel-S RAM resin as a solid support (0.24 meq/g). All amino acids used were dissolved in DMF to 0.2 mol concentration. A mixture of HOBT/HBTU 1:1 (0.5 mol/L) 4 eq. and DIPEA 4eq. was used to activate the amino acids. Fmoc-Cleavage was achieved with Piperidine in DMF (20%) for 3 min. Fmoc-cleavage was repeated.

Aloc-& Allyl-Cleavage:

The resin was treated manually with a solution of 20 eq. phenyl silane and 0.05 eq. of tetrakis triphenylphosphine palladium in DCM (5 ml) for 30 min at RT. This procedure was repeated. The resin was washed with a solution of 0.5% sodium dithiocarbamate in DMF twice. The washing step was repeated with DCM.

On-bead Cyclisation (Method A):

Again coupling-reagent (4 ml of an 0.5 mol/L solution HOBT/HBTU (1:1) and 1 ml of DIPEA (4 eq.) in DMF was added to the resin. The slurry was shaken for about 8 h at RT. The resin was washed with DMF and DCM twice. Completion of cyclisation was verified via Ninhydrin test.

Cleavage from Resin:

10 ml of the cleavage-cocktail (TFA; TIS; water (95/2.5/2.5)) was added to the resin and shaken for 1 h at RT. Cleaved peptide was precipitated in cold ether (−18° C.). The peptide was centrifuged and the precipitates washed twice with cold ether. The precipitate was dissolved in $H_2O$/Acetonitrile and lyophilized to yield 210 mg white powder.

All other analogues were generated upon Method B using the off-bead cyclisation strategy.

Off-bead Cyclisation (Method B):

Crude peptide was dissolved in DMF (15 ml). 1 eq of coupling reagents PyaOP (0.5 mol/L) in DMF and DIPEA in NMP (2 mol/l) were added. The reaction mixture was stirred at RT for 1 h. After the reaction was completed (LCMS control) the DMF content was concentrated down to approximately 2 ml. The residue was precipitated in cold (−18° C.) diethyl ether (40 ml). The peptide was centrifuged and the precipitate washed with cold ether.

Purification:

The crude peptide was purified by preparative HPLC on a Reprospher 100 C18-T Column (100×4.6 mm, 5 um particle size). As eluent system a mixture of 0.1% TFA/water/acetonitrile was used with a gradient of 0-50% acetonitrile within 0-30 min. The fractions were collected and checked by analytical HPLC. Fractions containing pure product were combined and lyophilized. 7.2 mg of white powder were obtained.

All other peptides listed below were synthesized accordingly.

Abbreviations:

Fmoc: 9-Fluorenylmethoxycarbonyl
tBu: tert. Butyl
Gly: Glycine
Phe: Phenylalanine
Cha: Cyclohexylalanine
Chg: Cyclohexylglycine
CyclopropGly: N-Cyclopropylglycine Sar: Sarcosine
Ile: Isoleucine
Leu: Leucine
Nle: Norleucin
Nva: Norvaline
Aib: Aminoisobutyric Acid
Pro: Proline
Ala: Alanine
Val: Valine
homoVal: Homovaline
MeVal: L-α-Methyl-Valine
His(Trt): sidechain-protected (Trityl) Histidine
Asn(Trt): sidechain-protected (Trityl)Asparagine
Gln(Trt): sidechain-protected (Trityl) Glutamine
Ser(tBu): sidechain-protected (tert. Butyl) Serine
Tyr(tBu): sidechain-protected (tBu)Tyrosine
Thr(tBu): sidechain-protected (tBu) Threonine
HOBT: N-Hydroxybenzotriazole
COMU: 1-[(1-(Cyano-2-ethoxy-2-oxoethylideneaminooxy) dimethylaminomorpholino)]uronium hexafluorophosphate
PyoAP: (7-Azabenzotriazol-1yloxy)tripyrrolidino-phosphonium hexaflourophosphate
HBTU: O-Benzotriazole-N,N,N',N'-tetramethyl-uronium-hexafluorophosphate
DMF: N,N-Dimethylformamide
NMP: N-Methylpyrrolidone
DIPEA: N,N-Diisopropylamine
DCM: Dichlormethane
MeCN: Acetonitril

EXAMPLE 1

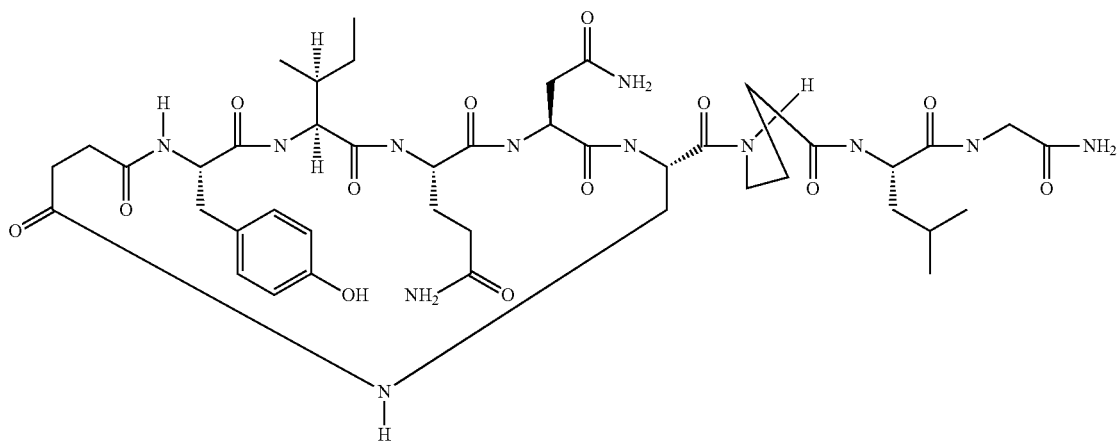 [SMILES: CC[C@H](C)[C@@H]1NC(=O)[C@H](Cc2ccc(O)cc2)NC(=O)CCC(=O)NC[C@@H](C(=O)N(C)CCCC(=O)N[C@@H](CC(C)C)C(=O)NCC(N)=O)NC(=O)[C@H](CC(N)=O)NC(=O)[C@H](CCC(N)=O)NC1=O]

The following amino acids were used: Fmoc-Gly-OH, Fmoc-Leu-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 971.1; observed 971.2

EXAMPLE 2

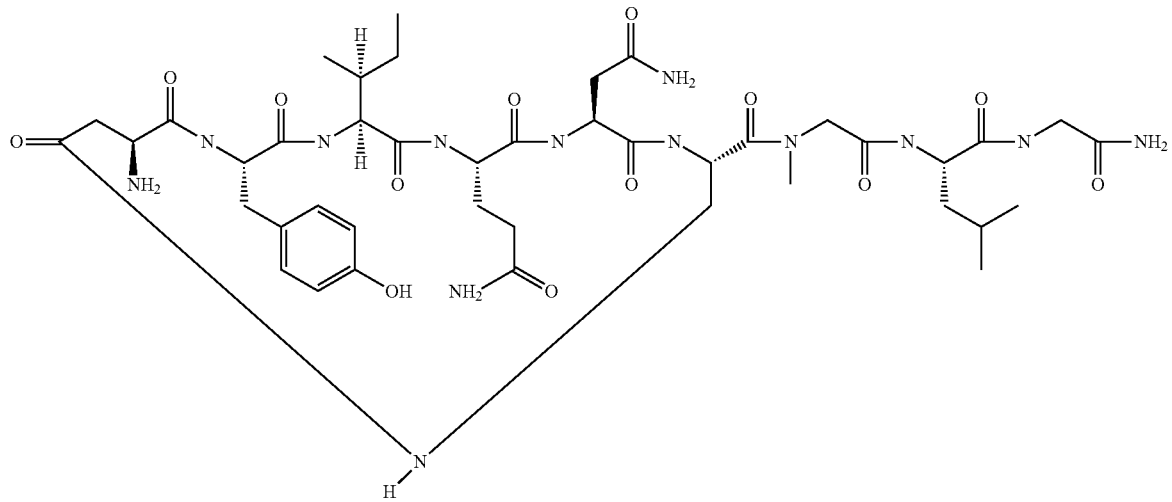 [SMILES: CC[C@H](C)[C@@H]1NC(=O)[C@H](Cc2ccc(O)cc2)NC(=O)[C@@H](N)CC(=O)NC[C@@H](C(=O)N(C)CC(=O)N[C@@H](CC(C)C)C(=O)NCC(N)=O)NC(=O)[C@H](CC(N)=O)NC(=O)[C@H](CCC(N)=O)NC1=O]

The following amino acids were used: Fmoc-Gly-OH, Fmoc-Leu-OH, Fmoc-Sar-OH, Fmoc-Dap(Aloc)-OH, Fmoc-Asn(Trt)-OH, Fmoc-Gln(Trt)-OH, Fmoc-Ile-OH, Fmoc-Tyr(tBu)-OH and Fmoc-Asp(Allyl)-OH. MS (M+H$^+$): expected 960.0; observed 960.8

EXAMPLE 3

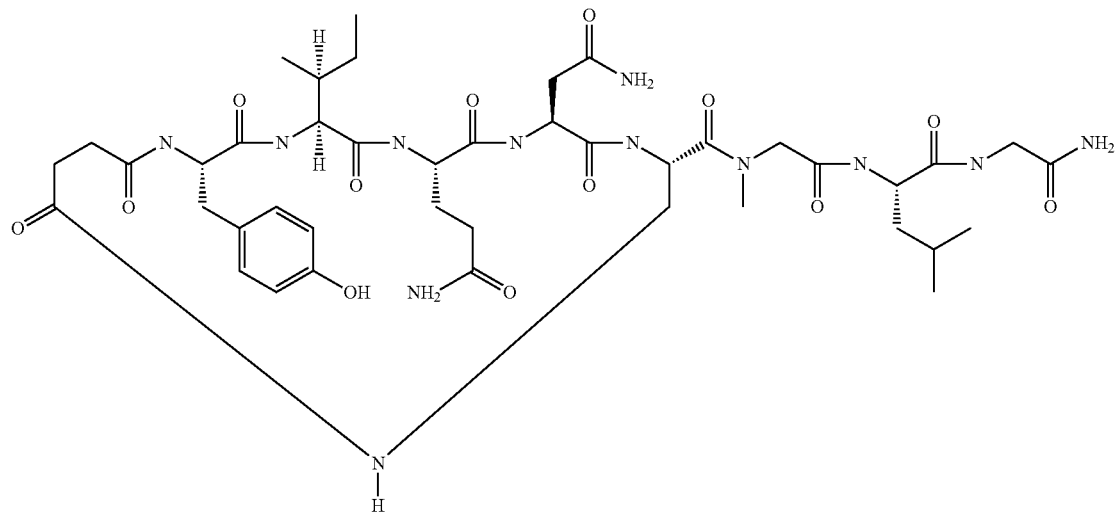 [SMILES: CC[C@H](C)[C@@H]1NC(=O)[C@H](Cc2ccc(O)cc2)NC(=O)CCC(=O)NC[C@@H](C(=O)N(C)CC(=O)N[C@@H](CC(C)C)C(=O)NCC(N)=O)NC(=O)[C@H](CC(N)=O)NC(=O)[C@H](CCC(N)=O)NC1=O]

The following amino acids were used: Fmoc-Gly-OH, Fmoc-Leu-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 945.0; observed 945.5

EXAMPLE 4

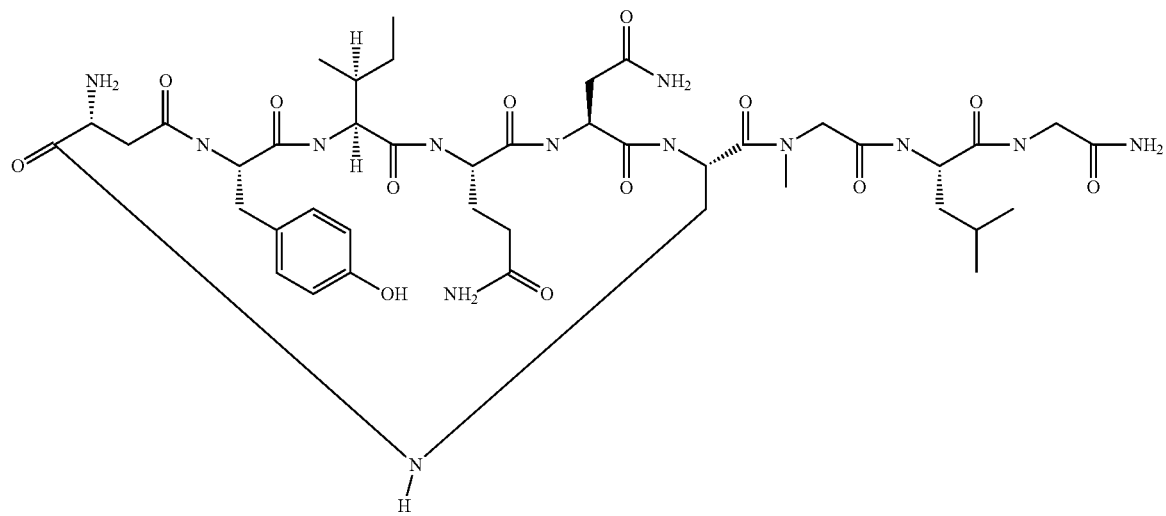 [SMILES: CC[C@H](C)[C@@H]1NC(=O)[C@H](Cc2ccc(O)cc2)NC(=O)C[C@@H](N)C(=O)NC[C@@H](C(=O)N(C)CC(=O)N[C@@H](CC(C)C)C(=O)NCC(N)=O)NC(=O)[C@H](CC(N)=O)NC(=O)[C@H](CCC(N)=O)NC1=O]

The following amino acids were used: Fmoc-Gly-OH, Fmoc-Leu-OH, Fmoc-SAR-OH, Fmoc-Dap(Aloc)-OH, Fmoc-Asn(Trt)-OH, Fmoc-Gln(Trt)-OH, Fmoc-Ile-OH, Fmoc-Tyr(tBu)-OH, Fmoc-D-AspOAllyl. MS (M+H$^+$): expected 960.0; observed 960.8

EXAMPLE 5

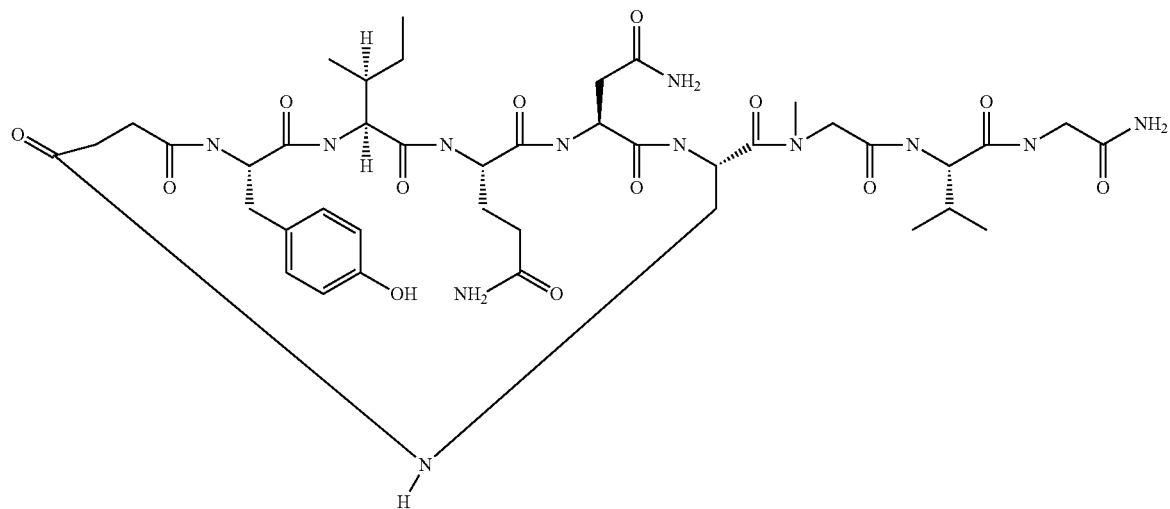 [SMILES: CC[C@H](C)[C@@H]1NC(=O)[C@H](Cc2ccc(O)cc2)NC(=O)CCC(=O)NC[C@@H](C(=O)N(C)CC(=O)N[C@H](C(=O)NCC(N)=O)C(C)C)NC(=O)[C@H](CC(N)=O)NC(=O)[C@H](CCC(N)=O)NC1=O]

The following amino acids were used: Fmoc-Gly-OH, Fmoc-Val-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 931.0; observed 931.1

EXAMPLE 6

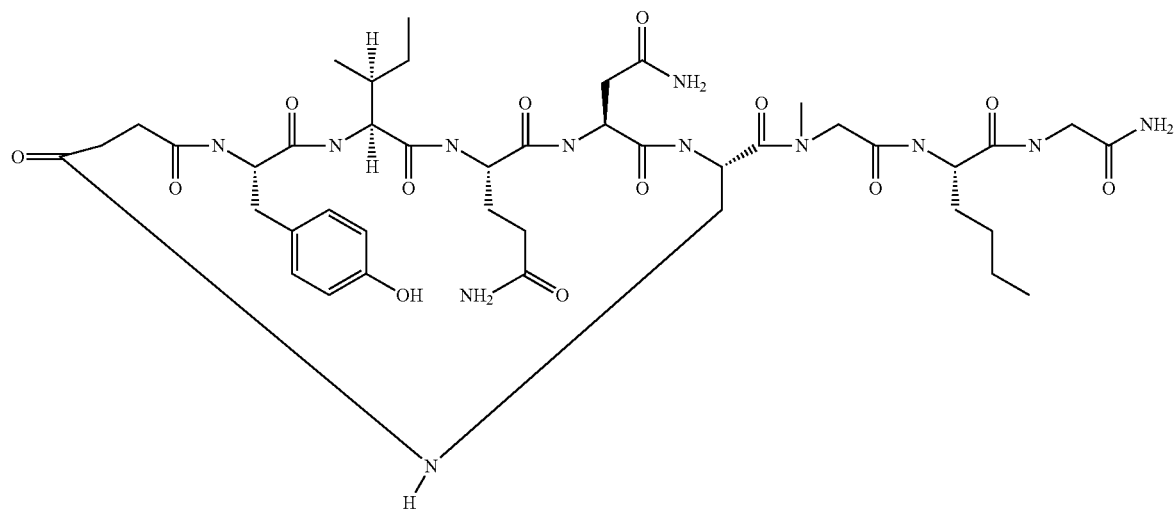 [SMILES: CCCC[C@H](NC(=O)CN(C)C(=O)[C@@H]1CNC(=O)CCC(=O)N[C@@H](Cc2ccc(O)cc2)C(=O)N[C@@H]([C@@H](C)CC)C(=O)N[C@@H](CCC(N)=O)C(=O)N[C@@H](CC(N)=O)C(=O)N1)C(=O)NCC(N)=O]

The following amino acids were used: Fmoc-Gly-OH, Fmoc-Nva-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 945.0; observed 945.2

EXAMPLE 7

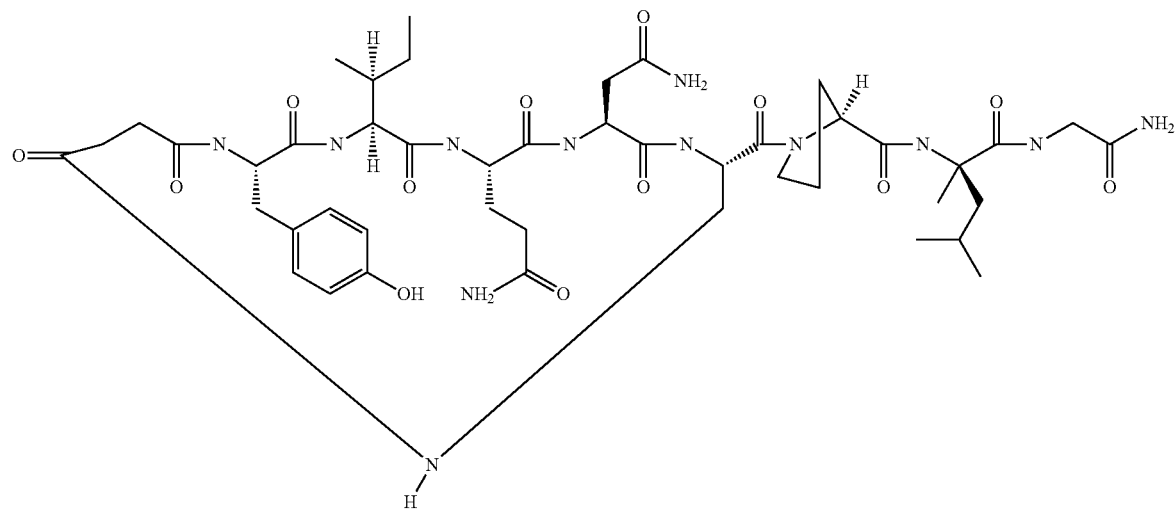

The following amino acids were used: Fmoc-Gly-OH, Fmoc-MeVal-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 985.0; observed 985.2

EXAMPLE 8

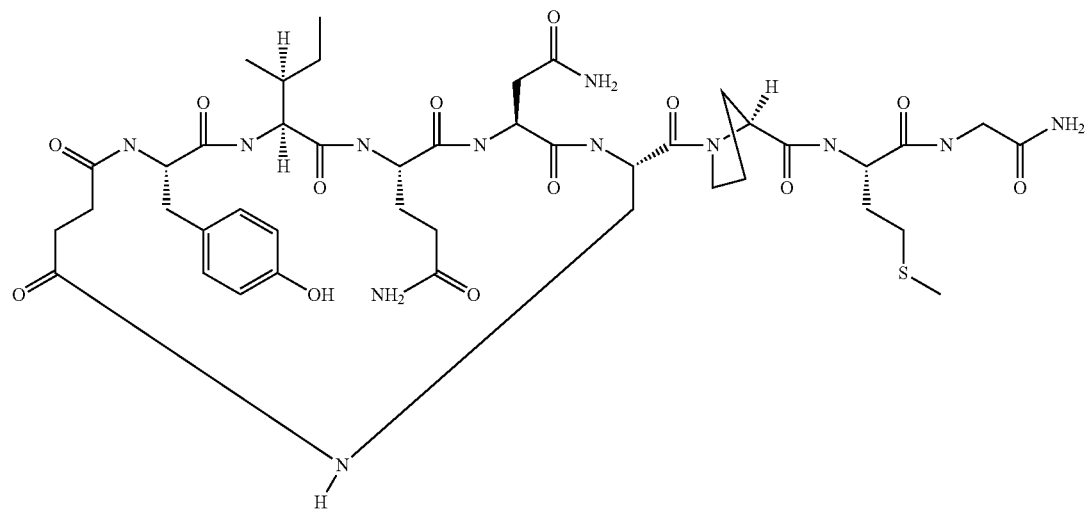

The following amino acids were used: Fmoc-Gly-OH, Fmoc-Met-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 989.1; observed 989.5

EXAMPLE 9

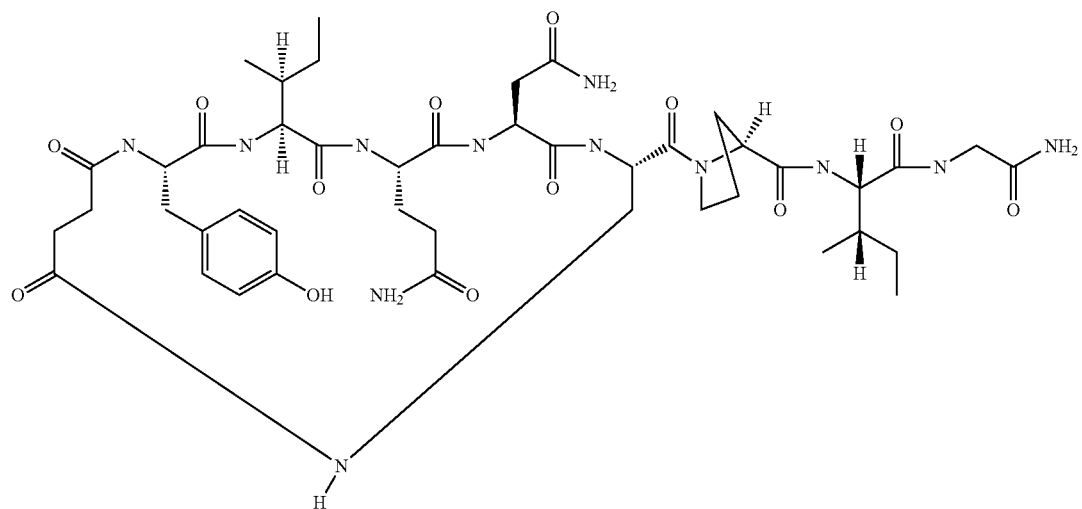

The following amino acids were used: Fmoc-Gly-OH, Fmoc-Ile-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 971.0; observed 971.5

EXAMPLE 10

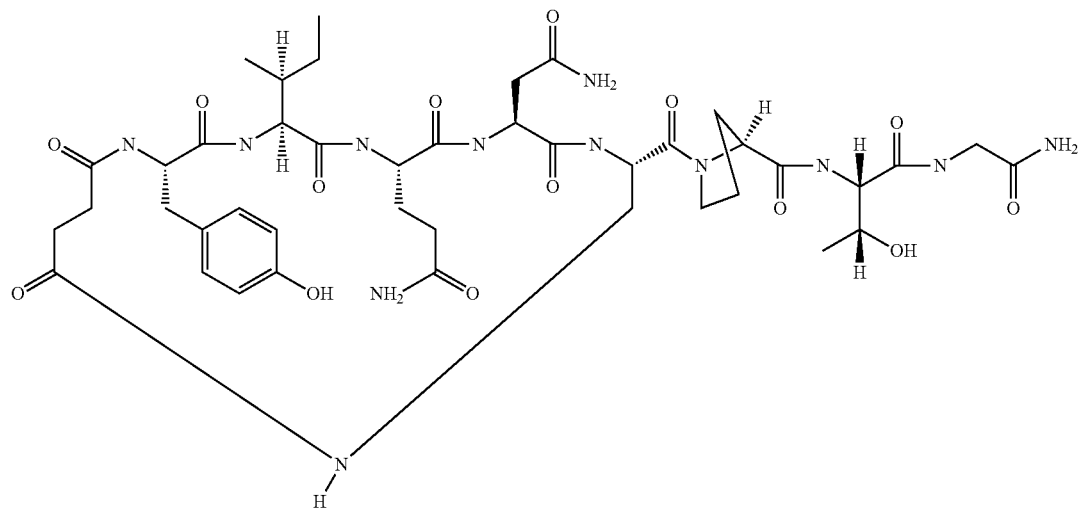

The following amino acids were used: Fmoc-Gly-OH, Fmoc-Thr(tBu)-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 959.0; observed 959.5

EXAMPLE 11

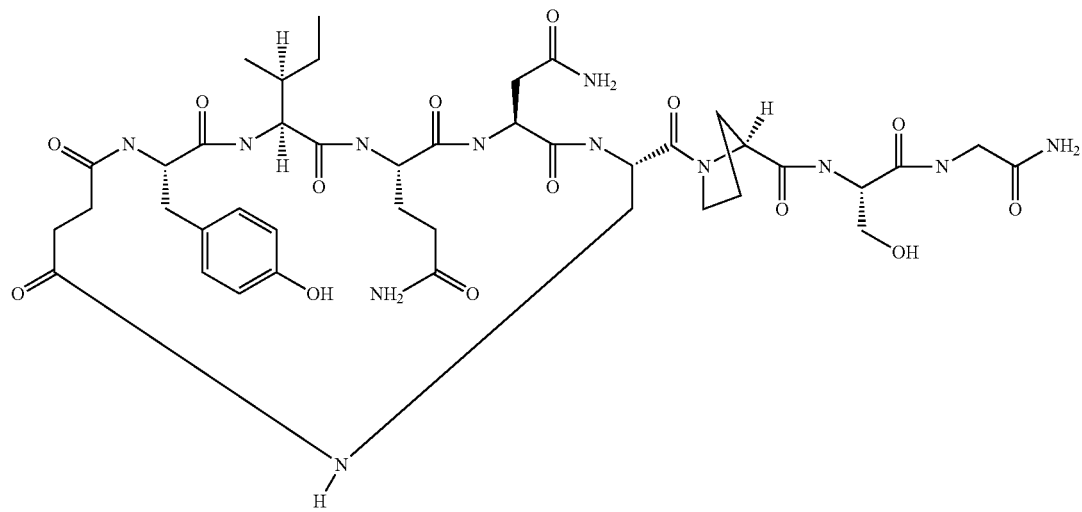

The following amino acids were used: Fmoc-Gly-OH, Fmoc-Ser(tBu)-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 945.0; observed 945.5

EXAMPLE 12

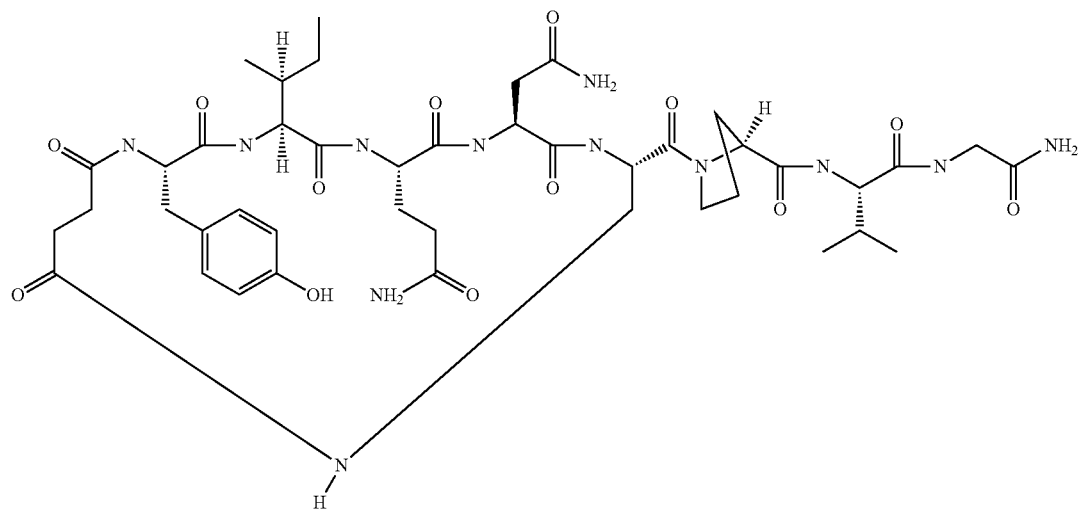

The following amino acids were used: Fmoc-Gly-OH, Fmoc-Val-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 957.0; observed 957.6

EXAMPLE 13

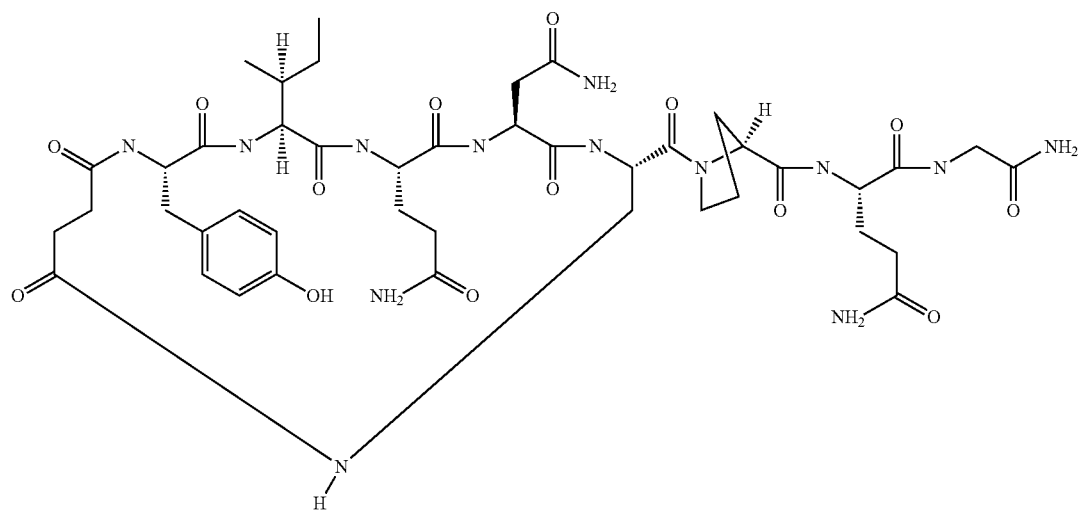

The following amino acids were used: Fmoc-Gly-OH, Fmoc-Gln(Trt)-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 986.0; observed 986.5

EXAMPLE 14

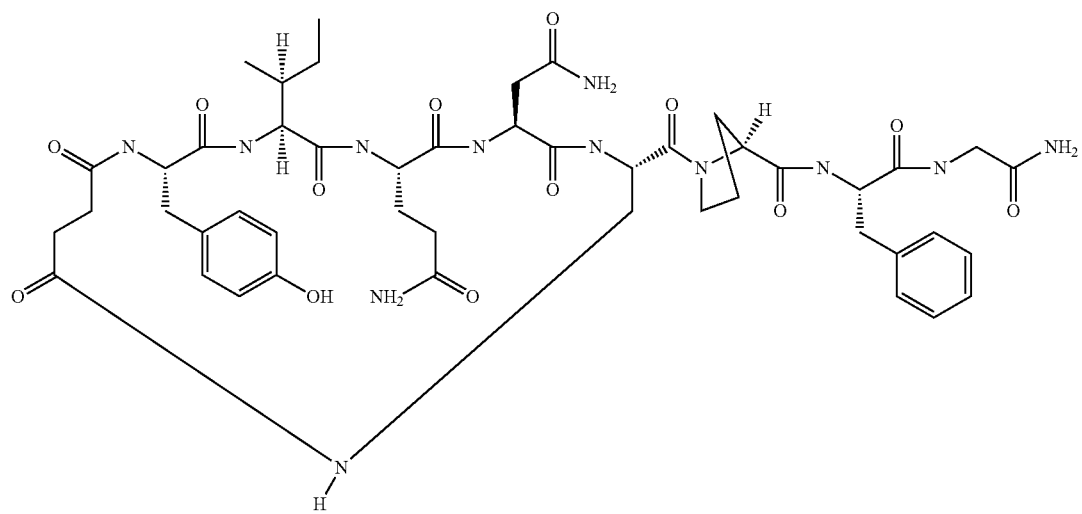

The following amino acids were used: Fmoc-Gly-OH, Fmoc-PheOH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 1005.0; observed 1006.8

EXAMPLE 15

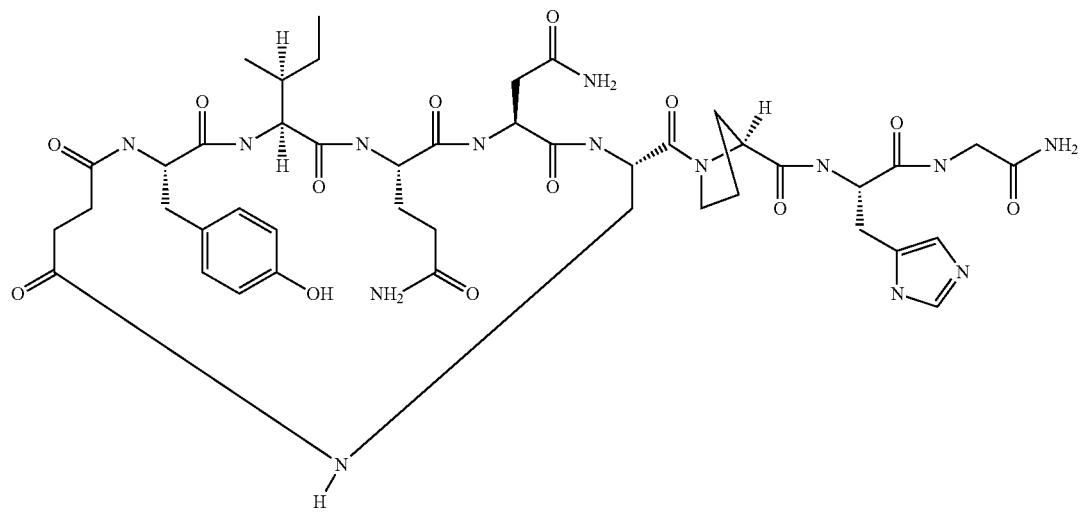

The following amino acids were used: Fmoc-Gly-OH, Fmoc-His(Trt)OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 995.0; observed 996.7

EXAMPLE 16

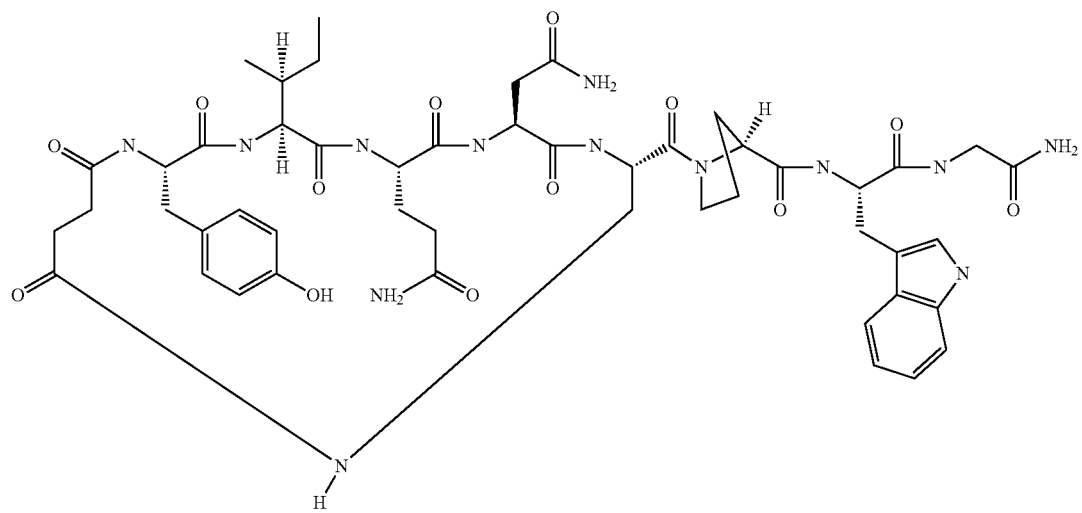

The following amino acids were used: Fmoc-Gly-OH, Fmoc-Trp(Boc)-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 1044.10; observed 1045.4

EXAMPLE 17

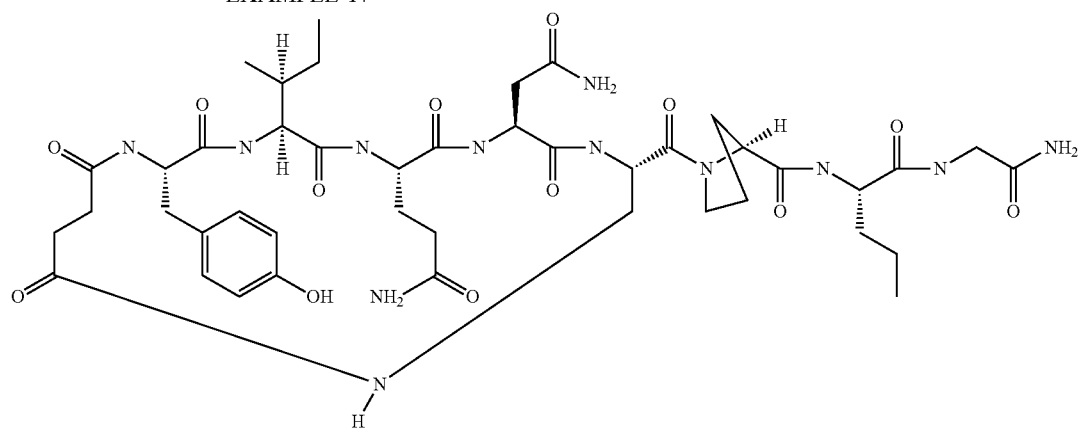

The following amino acids were used: Fmoc-Gly-OH, Fmoc-Nva-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 957.0; observed 957.5

EXAMPLE 18

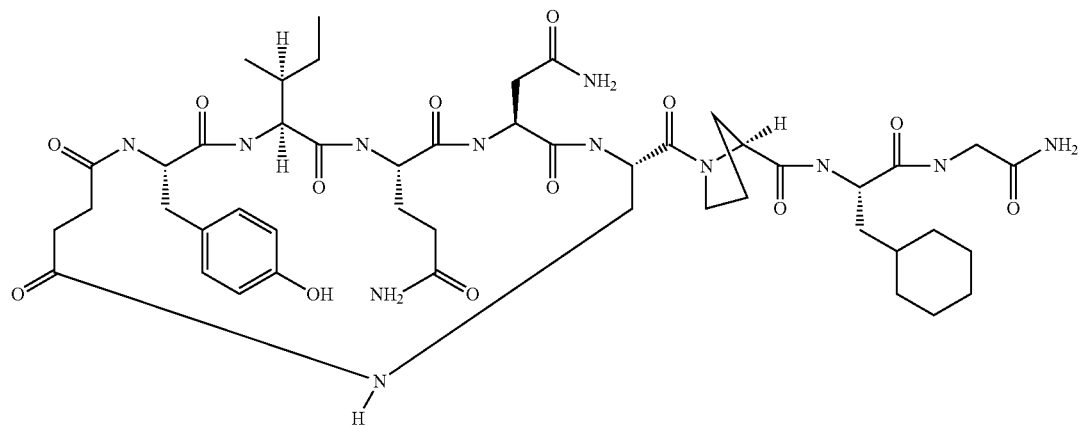

The following amino acids were used: Fmoc-Gly-OH, Fmoc-Cha-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 1011.1; observed 1011.5

EXAMPLE 19

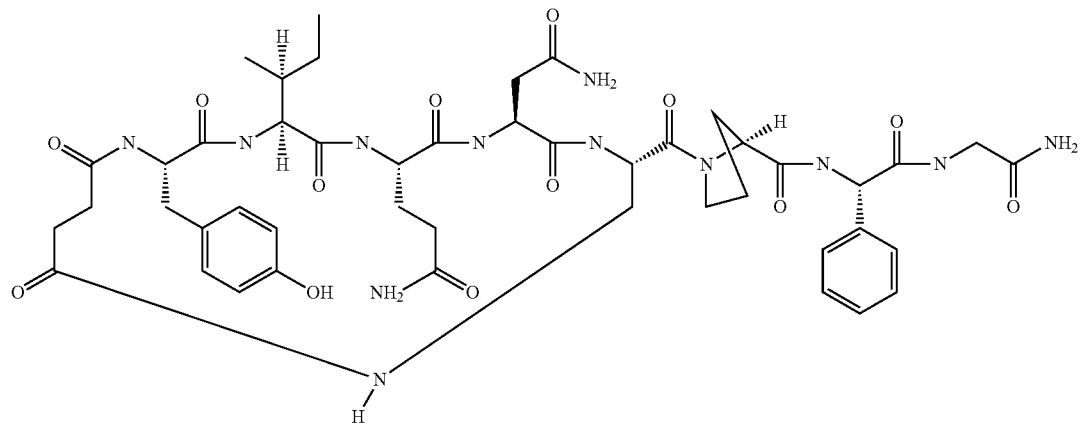

The following amino acids were used: Fmoc-Gly-OH, Fmoc-Phg-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H⁺): expected 991.0; observed 991.5

EXAMPLE 20

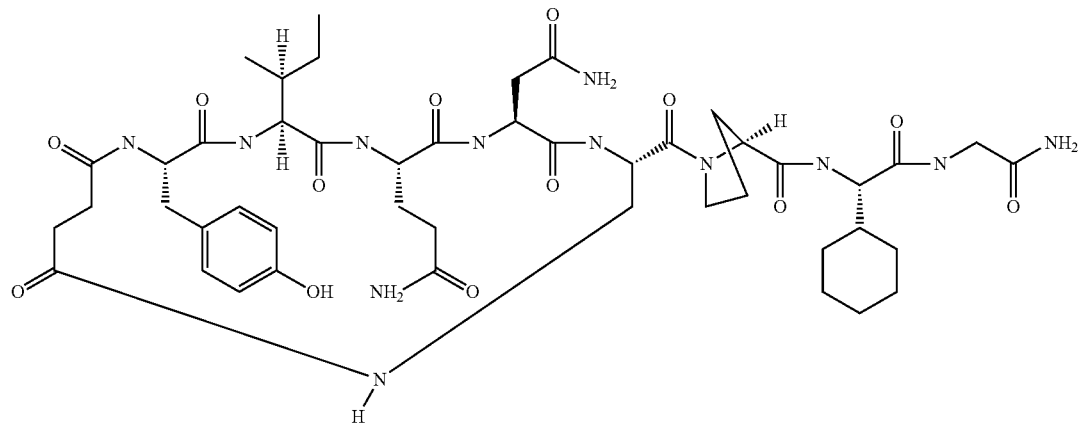

The following amino acids were used: Fmoc-Gly-OH, Fmoc-Chg-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H⁺): expected 997.0; observed 997.5

EXAMPLE 21

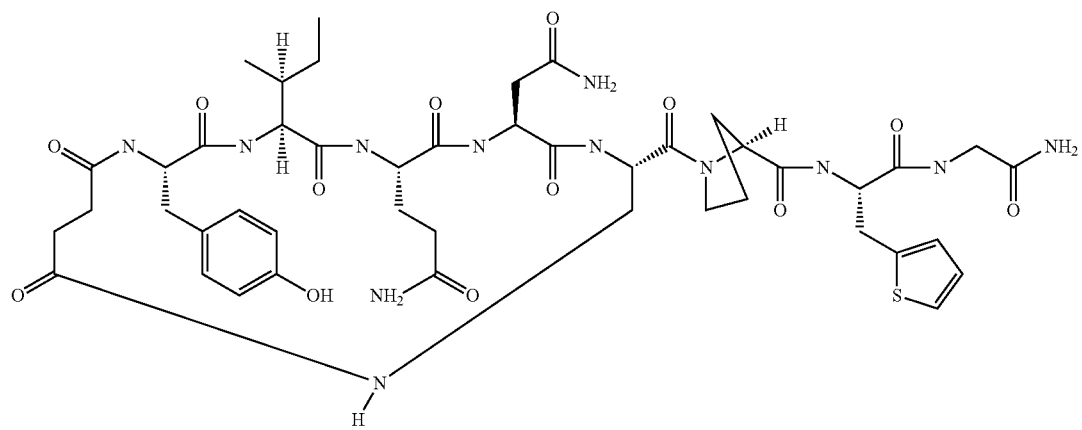

The following amino acids were used: Fmoc-Gly-OH, Fmoc-Thi-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H⁺): expected 1011.1; observed 1011.4

EXAMPLE 22

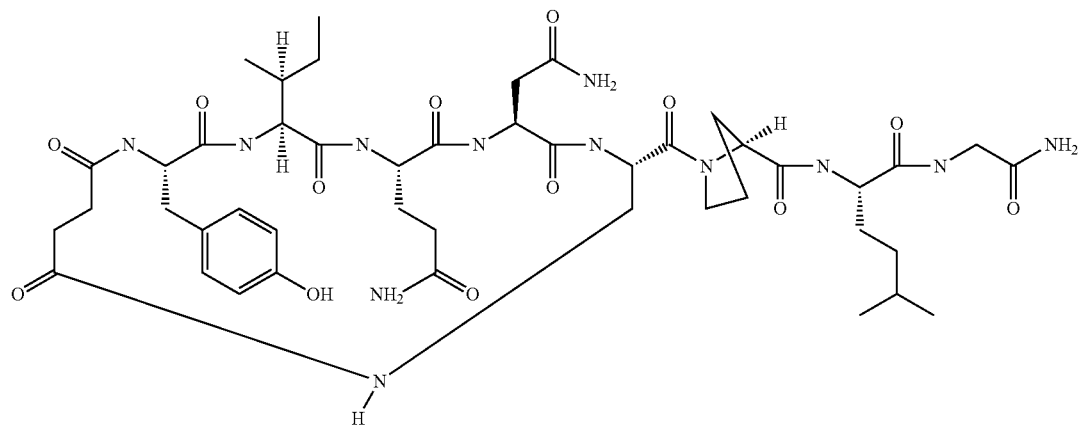

The following amino acids were used: Fmoc-Gly-OH, Fmoc-homoLeu-OH, Fmoc-Pro-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 985.1; observed 985.5

EXAMPLE 23

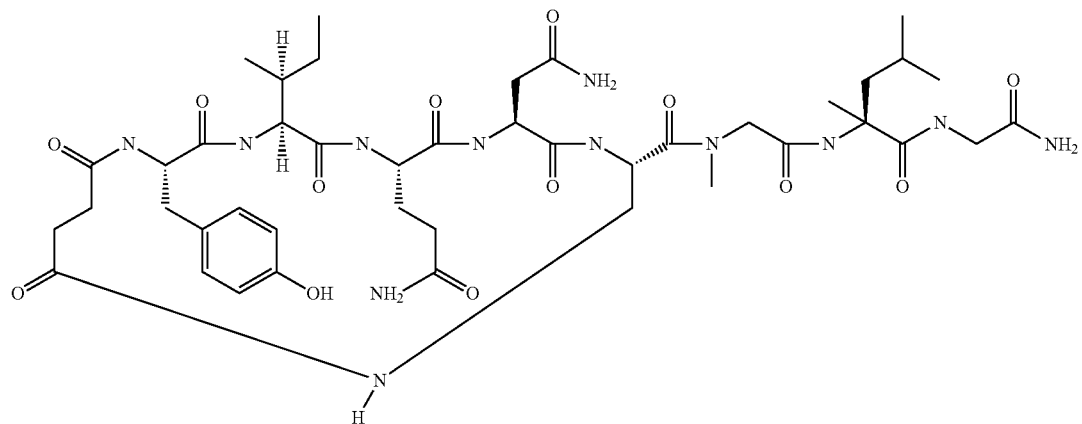 [SMILES: CC[C@H](C)[C@@H]1NC(=O)[C@H](Cc2ccc(O)cc2)NC(=O)CCC(=O)NC[C@@H](C(=O)N(C)CC(=O)N[C@@](C)(CC(C)C)C(=O)NCC(N)=O)NC(=O)[C@H](CC(N)=O)NC(=O)[C@H](CCC(N)=O)NC1=O]

The following amino acids were used: Fmoc-Gly-OH, Fmoc-MeLeu-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 959.0; observed 959.5

EXAMPLE 24

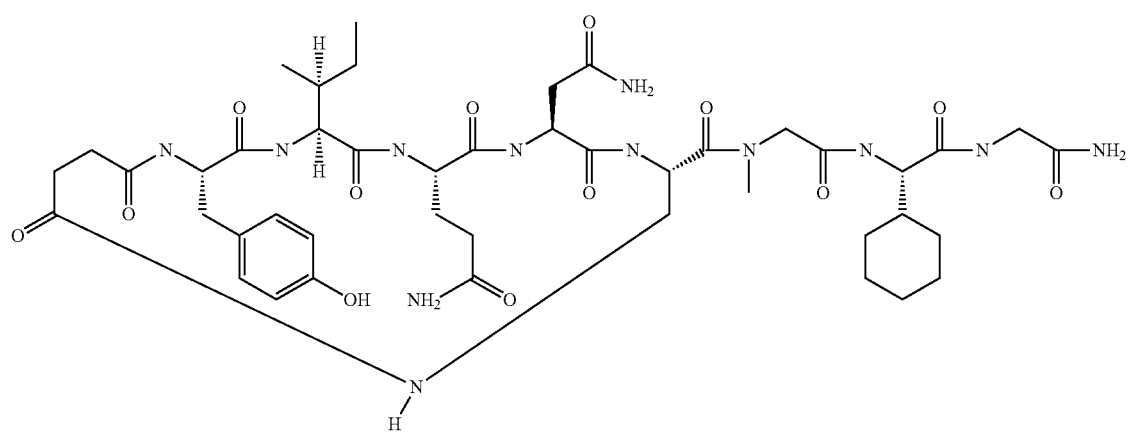 [SMILES: CC[C@H](C)[C@@H]1NC(=O)[C@H](Cc2ccc(O)cc2)NC(=O)CCC(=O)NC[C@@H](C(=O)N(C)CC(=O)N[C@H](C(=O)NCC(N)=O)C2CCCCC2)NC(=O)[C@H](CC(N)=O)NC(=O)[C@H](CCC(N)=O)NC1=O]

The following amino acids were used: Fmoc-Gly-OH, Fmoc-Chg-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 971.0; observed 971.2

EXAMPLE 25

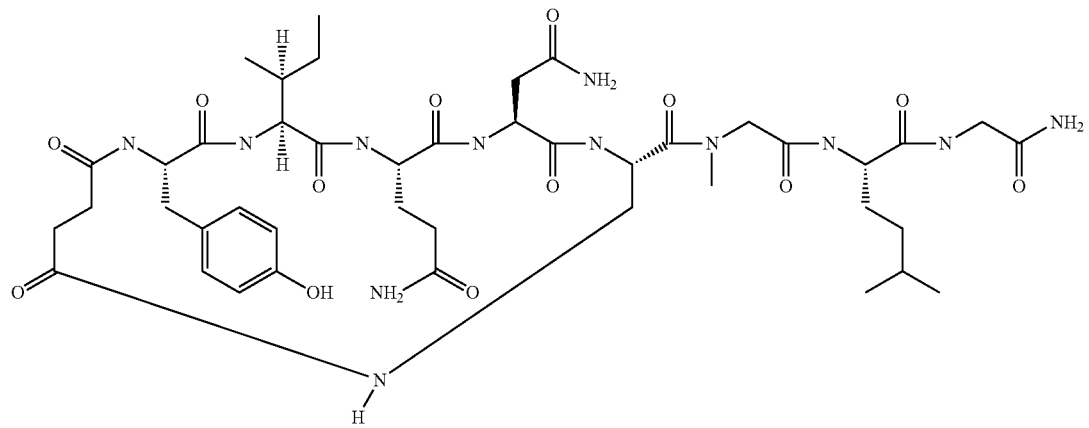 [SMILES: CC[C@H](C)[C@@H]1NC(=O)[C@H](Cc2ccc(O)cc2)NC(=O)CCC(=O)NC[C@@H](C(=O)N(C)CC(=O)N[C@@H](CCC(C)C)C(=O)NCC(N)=O)NC(=O)[C@H](CC(N)=O)NC(=O)[C@H](CCC(N)=O)NC1=O]

The following amino acids were used: Fmoc-Gly-OH, Fmoc-homoLeu-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 959.0; observed 959.1

EXAMPLE 26

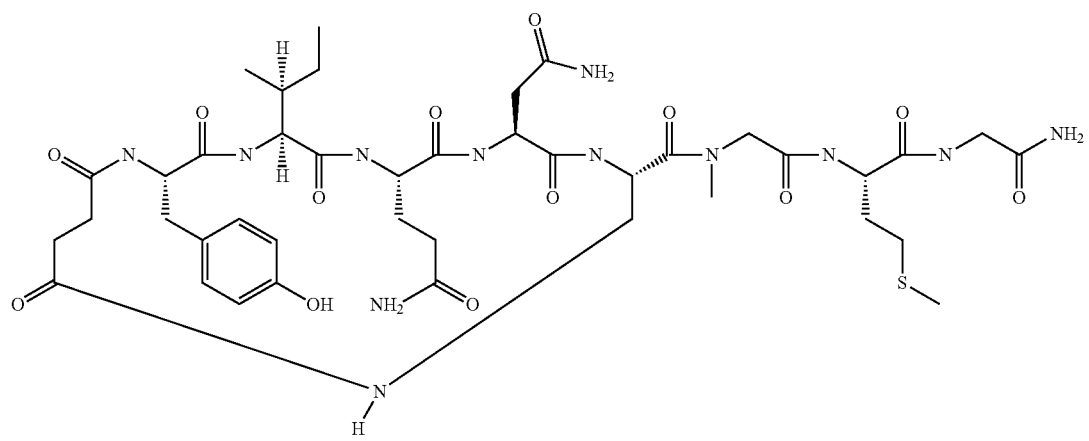 [SMILES: CC[C@H](C)[C@@H]1NC(=O)[C@H](Cc2ccc(O)cc2)NC(=O)CCC(=O)NC[C@@H](C(=O)N(C)CC(=O)N[C@@H](CCSC)C(=O)NCC(N)=O)NC(=O)[C@H](CC(N)=O)NC(=O)[C@H](CCC(N)=O)NC1=O]

The following amino acids were used: Fmoc-Gly-OH, Fmoc-Met-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 963.1; observed 963.6

EXAMPLE 27

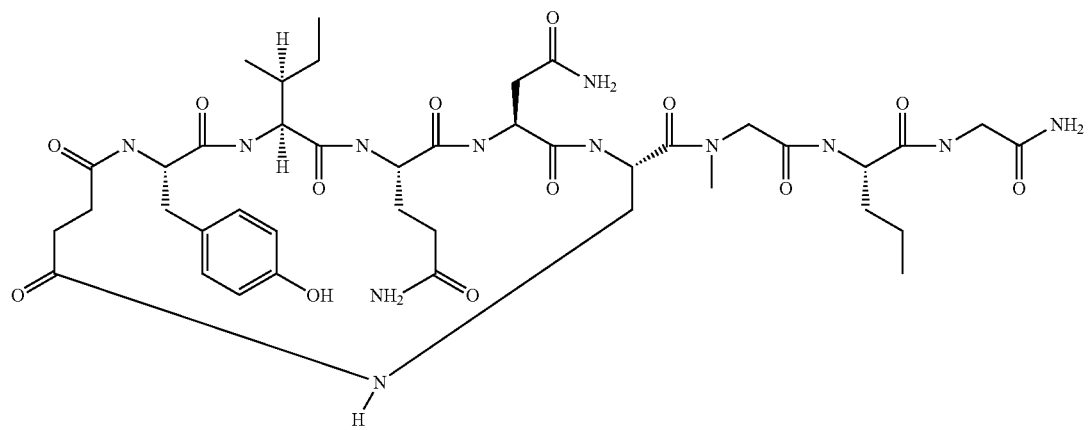 [SMILES: CCC[C@H](NC(=O)CN(C)C(=O)[C@@H]1CNC(=O)CCC(=O)N[C@@H](Cc2ccc(O)cc2)C(=O)N[C@@H]([C@@H](C)CC)C(=O)N[C@@H](CCC(N)=O)C(=O)N[C@@H](CC(N)=O)C(=O)N1)C(=O)NCC(N)=O]

The following amino acids were used: Fmoc-Gly-OH, Fmoc-Nva-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 931.0; observed 931.5

EXAMPLE 28

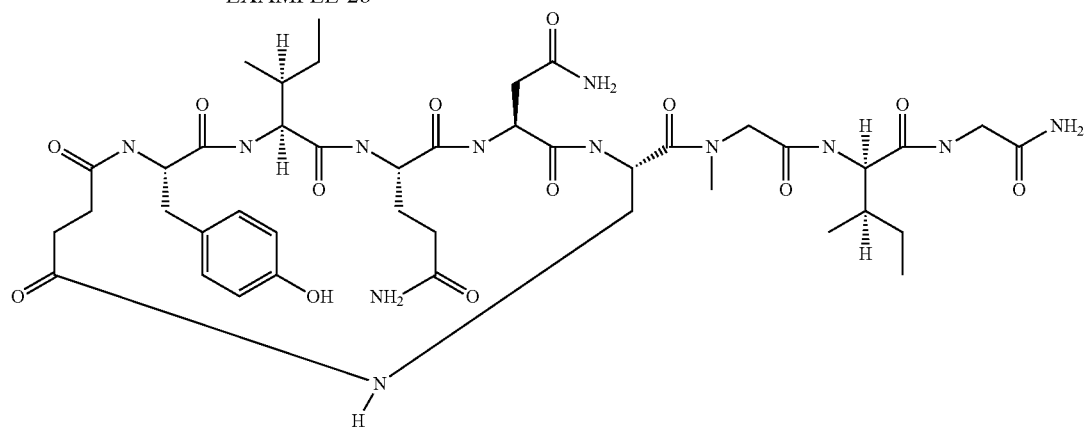

The following amino acids were used: Fmoc-Gly-OH, Fmoc-Ile-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 945.0; observed 945.5

EXAMPLE 29

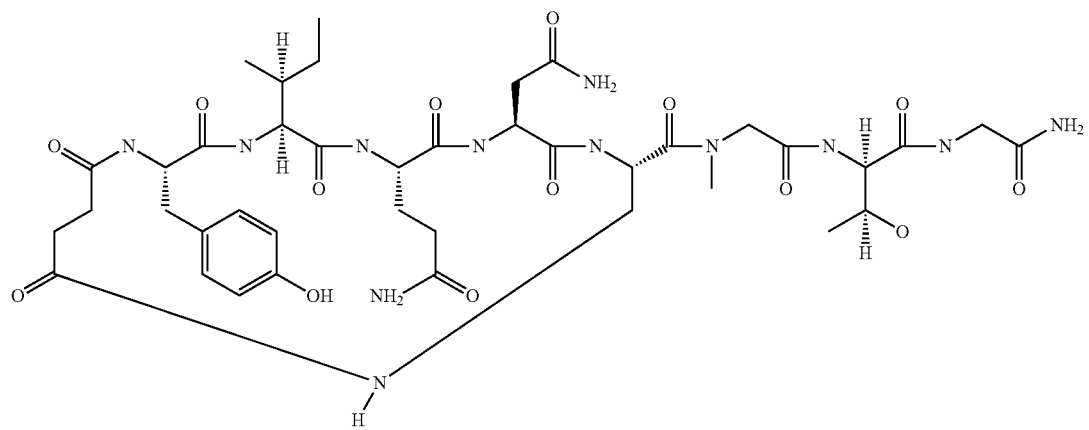 [SMILES: CC[C@H](C)[C@@H]1NC(=O)[C@H](Cc2ccc(O)cc2)NC(=O)CCC(=O)NC[C@@H](C(=O)N(C)CC(=O)N[C@@H](C(=O)NCC(N)=O)[C@H](C)O)NC(=O)[C@H](CC(N)=O)NC(=O)[C@H](CCC(N)=O)NC1=O]

The following amino acids were used: Fmoc-Gly-OH, Fmoc-Thr(tBu)-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 933.0; observed 933.6

EXAMPLE 30

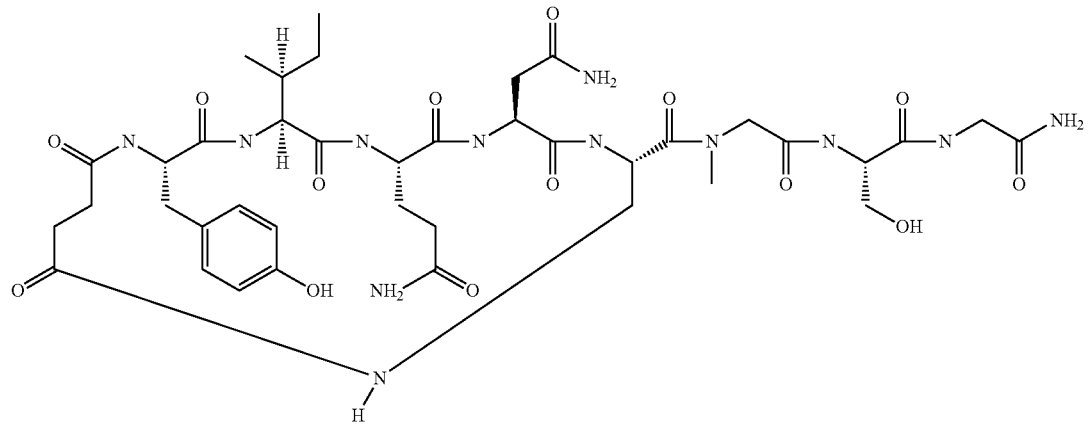 [SMILES: CC[C@H](C)[C@@H]1NC(=O)[C@H](Cc2ccc(O)cc2)NC(=O)CCC(=O)NC[C@@H](C(=O)N(C)CC(=O)N[C@@H](CO)C(=O)NCC(N)=O)NC(=O)[C@H](CC(N)=O)NC(=O)[C@H](CCC(N)=O)NC1=O]

The following amino acids were used: Fmoc-Gly-OH, Fmoc-Ser(tBu)-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 919.0; observed 919.4

EXAMPLE 31

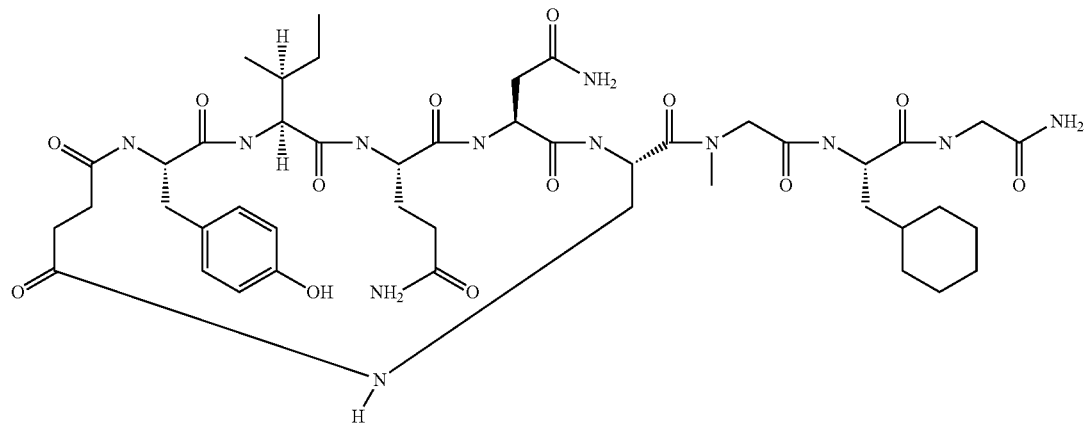 [SMILES: CC[C@H](C)[C@@H]1NC(=O)[C@H](Cc2ccc(O)cc2)NC(=O)CCC(=O)NC[C@@H](C(=O)N(C)CC(=O)N[C@@H](CC2CCCCC2)C(=O)NCC(N)=O)NC(=O)[C@H](CC(N)=O)NC(=O)[C@H](CCC(N)=O)NC1=O]

The following amino acids were used: Fmoc-Gly-OH, Fmoc-Cha-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 985.1; observed 985.6

EXAMPLE 32

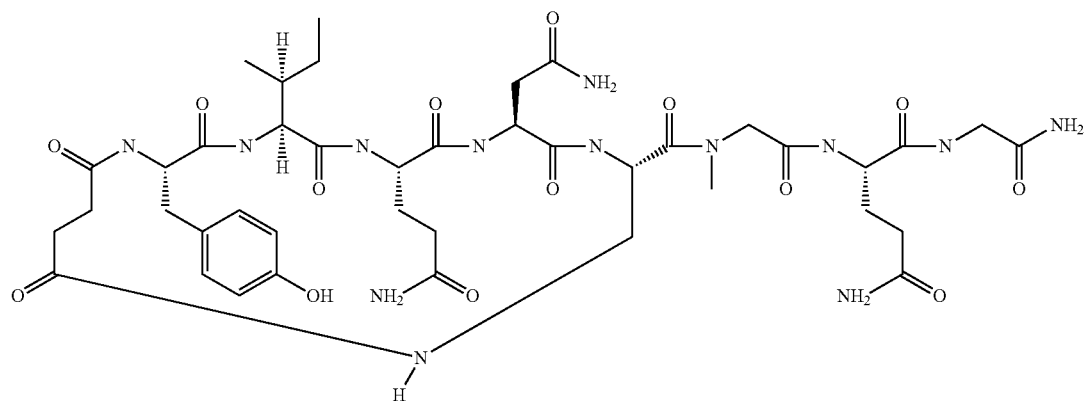 [SMILES: CC[C@H](C)[C@@H]1NC(=O)[C@H](Cc2ccc(O)cc2)NC(=O)CCC(=O)NC[C@@H](C(=O)N(C)CC(=O)N[C@@H](CCC(N)=O)C(=O)NCC(N)=O)NC(=O)[C@H](CC(N)=O)NC(=O)[C@H](CCC(N)=O)NC1=O]

The following amino acids were used: Fmoc-Gly-OH, Fmoc-Gln(Trt)-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 960.0; observed 960.8

EXAMPLE 33

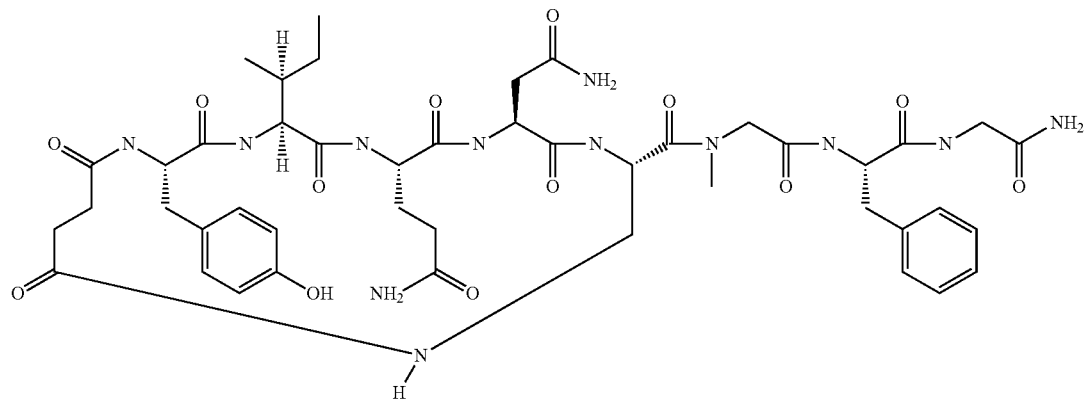 [SMILES: CC[C@H](C)[C@@H]1NC(=O)[C@H](Cc2ccc(O)cc2)NC(=O)CCC(=O)NC[C@@H](C(=O)N(C)CC(=O)N[C@@H](Cc2ccccc2)C(=O)NCC(N)=O)NC(=O)[C@H](CC(N)=O)NC(=O)[C@H](CCC(N)=O)NC1=O]

The following amino acids were used: Fmoc-Gly-OH, Fmoc-Phe-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 979.0; observed 979.3

EXAMPLE 34

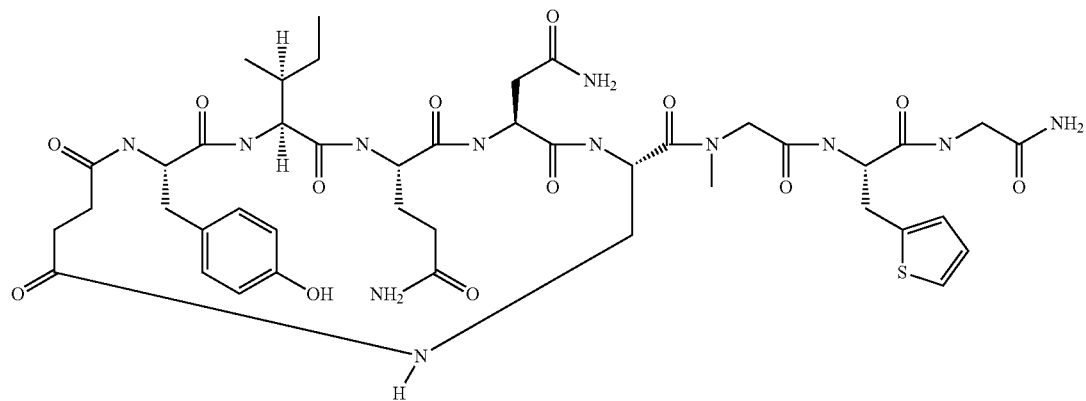 [SMILES: CC[C@H](C)[C@@H]1NC(=O)[C@H](Cc2ccc(O)cc2)NC(=O)CCC(=O)NC[C@@H](C(=O)N(C)CC(=O)N[C@@H](Cc2cccs2)C(=O)NCC(N)=O)NC(=O)[C@H](CC(N)=O)NC(=O)[C@H](CCC(N)=O)NC1=O]

The following amino acids were used: Fmoc-Gly-OH, Fmoc-Thi-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 985.1; observed 985.6

EXAMPLE 35

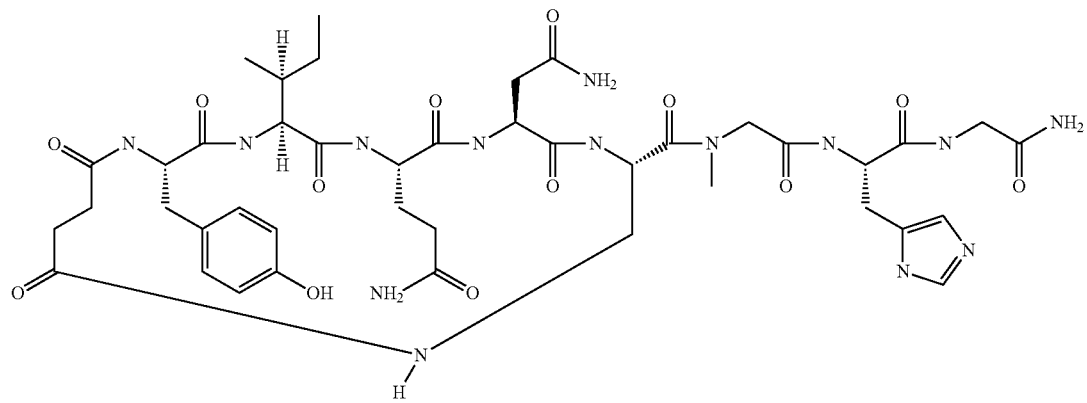 [SMILES: CC[C@H](C)[C@@H]1NC(=O)[C@H](Cc2ccc(O)cc2)NC(=O)CCC(=O)NC[C@@H](C(=O)N(C)CC(=O)N[C@@H](Cc2cnc[nH]2)C(=O)NCC(N)=O)NC(=O)[C@H](CC(N)=O)NC(=O)[C@H](CCC(N)=O)NC1=O]

The following amino acids were used: Fmoc-Gly-OH, Fmoc-His(Trt)-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 969.0; observed 969.9

EXAMPLE 36

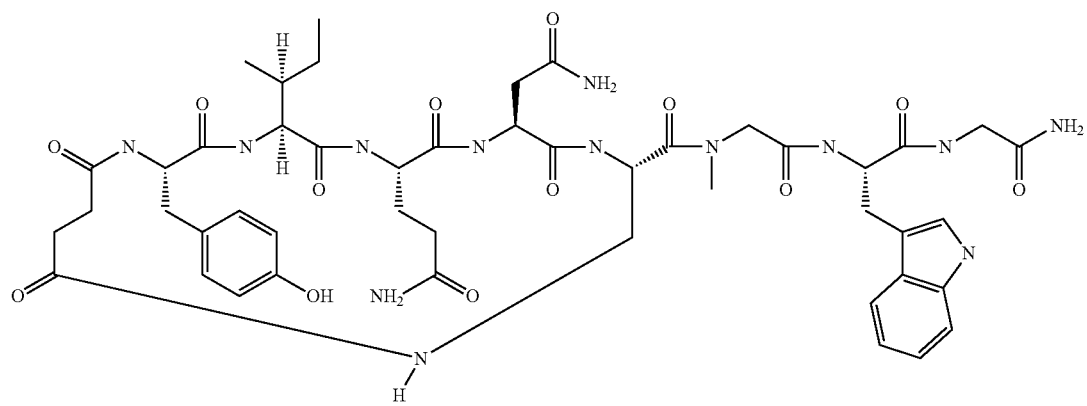 [SMILES: CC[C@H](C)[C@@H]1NC(=O)[C@H](Cc2ccc(O)cc2)NC(=O)CCC(=O)NC[C@@H](C(=O)N(C)CC(=O)N[C@@H](Cc2c[nH]c3ccccc23)C(=O)NCC(N)=O)NC(=O)[C@H](CC(N)=O)NC(=O)[C@H](CCC(N)=O)NC1=O]

The following amino acids were used: Fmoc-Gly-OH, Fmoc-Trp(Boc)-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 1018.0; observed 1018.6

EXAMPLE 37

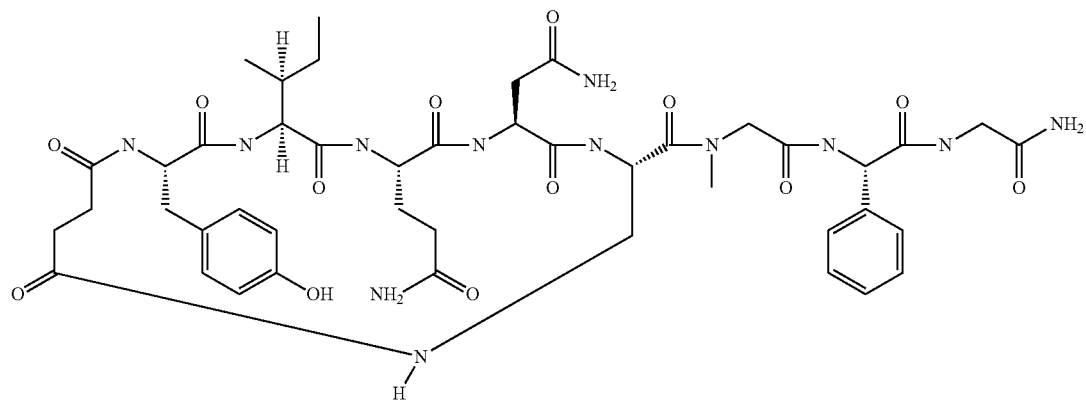 [SMILES: CC[C@H](C)[C@@H]1NC(=O)[C@H](Cc2ccc(O)cc2)NC(=O)CCC(=O)NC[C@@H](C(=O)N(C)CC(=O)N[C@H](C(=O)NCC(N)=O)c2ccccc2)NC(=O)[C@H](CC(N)=O)NC(=O)[C@H](CCC(N)=O)NC1=O]

The following amino acids were used: Fmoc-Gly-OH, Fmoc-Phg-OH, Fmoc-Sar-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate. MS (M+H$^+$): expected 965.0; observed 965.2

EXAMPLE 38

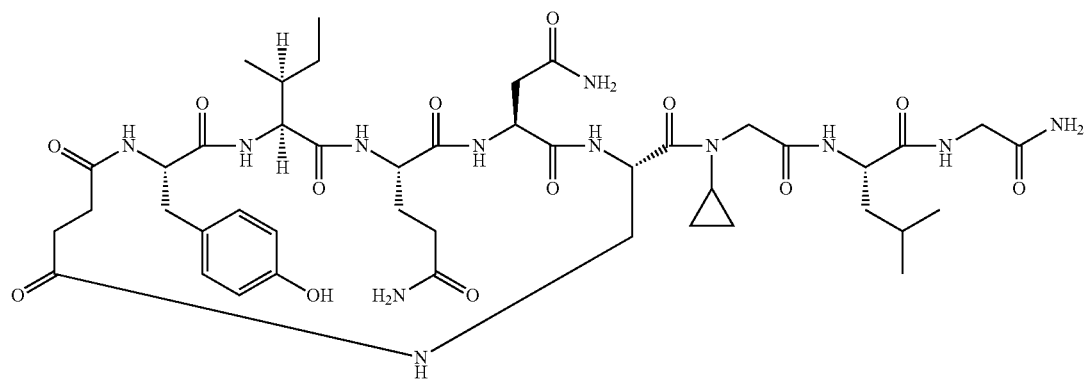 [SMILES: CC[C@H](C)[C@@H]1NC(=O)[C@H](Cc2ccc(O)cc2)NC(=O)CCC(=O)NC[C@@H](C(=O)N(CC(=O)N[C@@H](CC(C)C)C(=O)NCC(N)=O)C2CC2)NC(=O)[C@H](CC(N)=O)NC(=O)[C@H](CCC(N)=O)NC1=O]

The following amino acids were used: Fmoc-Gly-OH, Fmoc-Leu-OH, Fmoc-CyclopropGly-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate.
MS (M+H$^+$): expected 971.1; observed 971.8

EXAMPLE 39

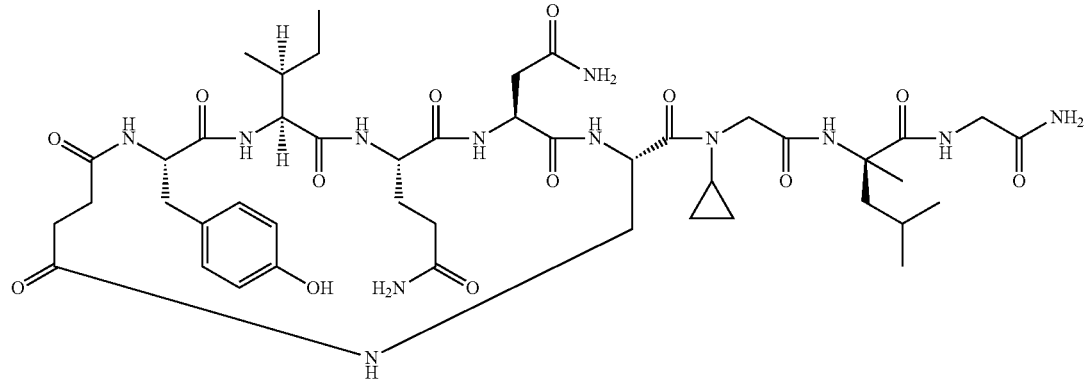 [SMILES: CC[C@H](C)[C@@H]1NC(=O)[C@H](Cc2ccc(O)cc2)NC(=O)CCC(=O)NC[C@@H](C(=O)N(CC(=O)N[C@](C)(CC(C)C)C(=O)NCC(N)=O)C2CC2)NC(=O)[C@H](CC(N)=O)NC(=O)[C@H](CCC(N)=O)NC1=O]

The following amino acids were used: Fmoc-Gly-OH, Fmoc-MeVal-OH, Fmoc-CyclopropGly-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate.

MS (M+H$^+$): expected 985.1; observed 985.6

EXAMPLE 40

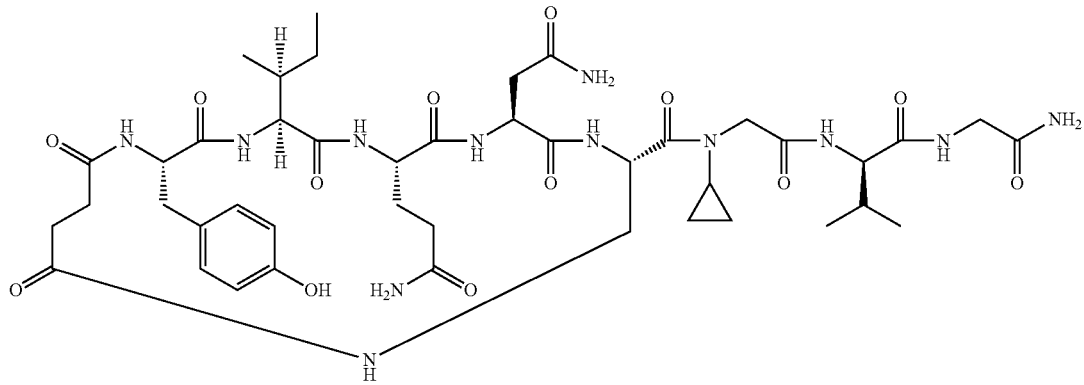 [SMILES: CC[C@H](C)[C@@H]1NC(=O)[C@H](Cc2ccc(O)cc2)NC(=O)CCC(=O)NC[C@@H](C(=O)N(CC(=O)N[C@@H](C(=O)NCC(N)=O)C(C)C)C2CC2)NC(=O)[C@H](CC(N)=O)NC(=O)[C@H](CCC(N)=O)NC1=O]

The following amino acids were used: Fmoc-Gly-OH, Fmoc-Val-OH, Fmoc-CyclopropGly-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate.

MS (M+H$^+$): expected 957.0; observed 957.5

EXAMPLE 41

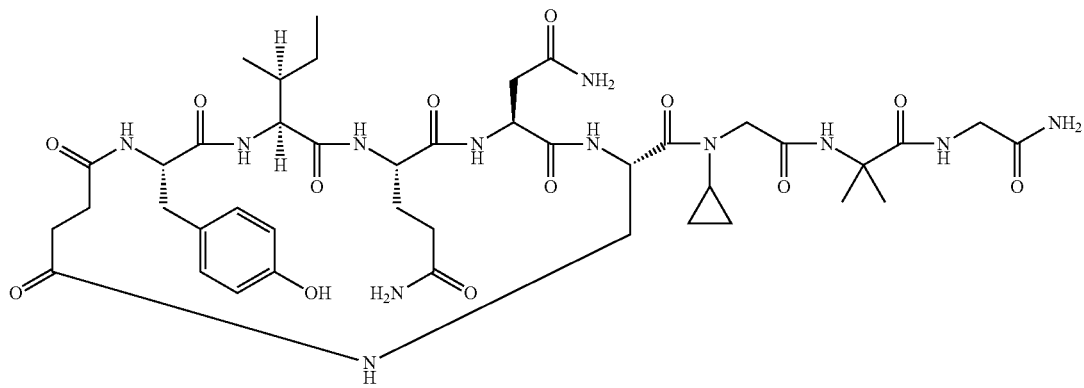 [SMILES: CC[C@H](C)[C@@H]1NC(=O)[C@H](Cc2ccc(O)cc2)NC(=O)CCC(=O)NC[C@@H](C(=O)N(CC(=O)NC(C)(C)C(=O)NCC(N)=O)C2CC2)NC(=O)[C@H](CC(N)=O)NC(=O)[C@H](CCC(N)=O)NC1=O]

The following amino acids were used: Fmoc-Gly-OH, Fmoc-Aib-OH, Fmoc-CyclopropGly-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate.

MS (M+H$^+$): expected 943.0; observed 943.5

EXAMPLE 42

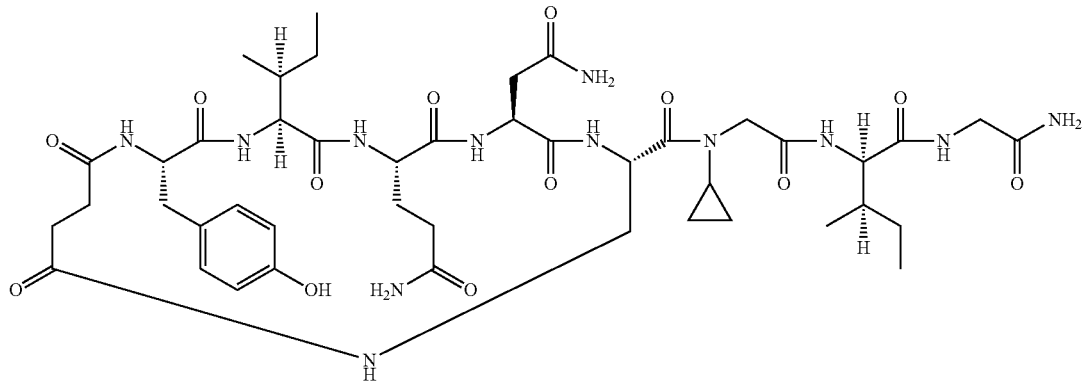 [SMILES: CC[C@@H](C)[C@@H](NC(=O)CN(C(=O)[C@@H]1CNC(=O)CCC(=O)N[C@@H](Cc2ccc(O)cc2)C(=O)N[C@@H]([C@@H](C)CC)C(=O)N[C@@H](CCC(N)=O)C(=O)N[C@@H](CC(N)=O)C(=O)N1)C1CC1)C(=O)NCC(N)=O]

The following amino acids were used: Fmoc-Gly-OH, Fmoc-Ile-OH, Fmoc-CyclopropGly-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate.

MS (M+H$^+$): expected 971.1; observed 971.6

EXAMPLE 43

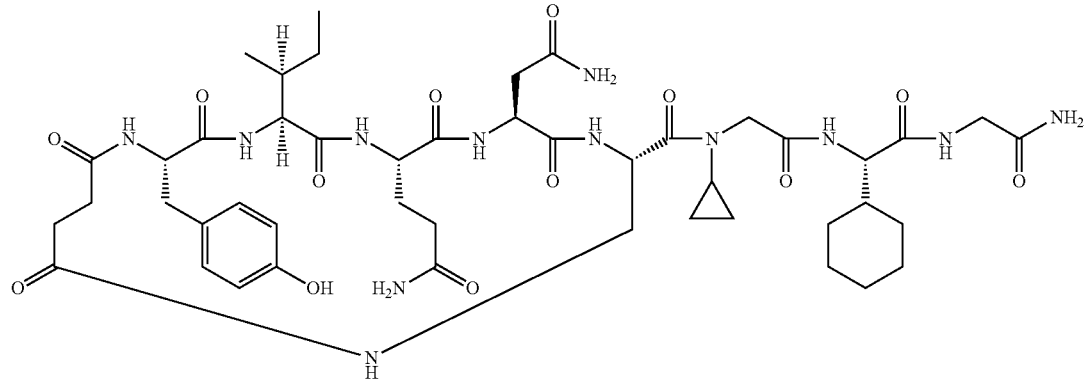 [SMILES: CC[C@H](C)[C@@H]1NC(=O)[C@H](Cc2ccc(O)cc2)NC(=O)CCC(=O)NC[C@@H](C(=O)N(CC(=O)N[C@H](C(=O)NCC(N)=O)C2CCCCC2)C2CC2)NC(=O)[C@H](CC(N)=O)NC(=O)[C@H](CCC(N)=O)NC1=O]

The following amino acids were used: Fmoc-Gly-OH, Fmoc-Chg-OH, Fmoc-CyclopropGly-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate.

MS (M+H$^+$): expected 997.1; observed 997.6

EXAMPLE 44

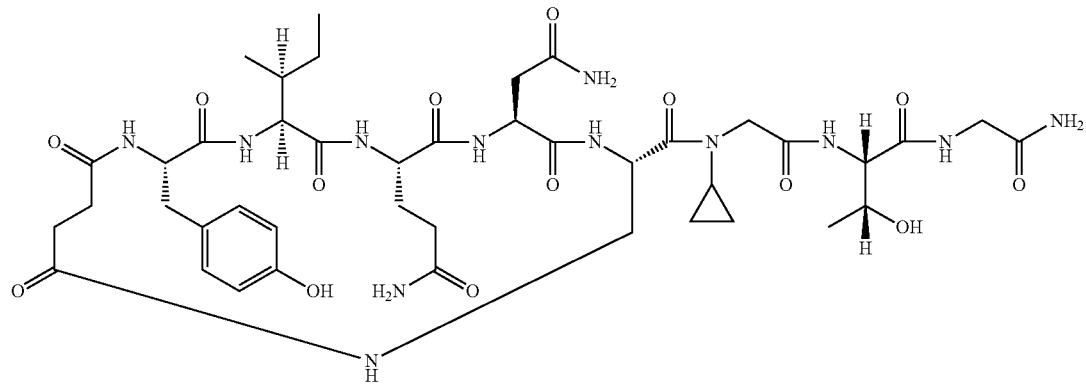 [SMILES: CC[C@H](C)[C@@H]1NC(=O)[C@H](Cc2ccc(O)cc2)NC(=O)CCC(=O)NC[C@@H](C(=O)N(CC(=O)N[C@H](C(=O)NCC(N)=O)[C@@H](C)O)C2CC2)NC(=O)[C@H](CC(N)=O)NC(=O)[C@H](CCC(N)=O)NC1=O]

The following amino acids were used: Fmoc-Gly-OH, Fmoc-Thr(tBu)-OH, Fmoc-CyclopropGly-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate.

MS (M+H$^+$): expected 959.0; observed 959.5

EXAMPLE 45

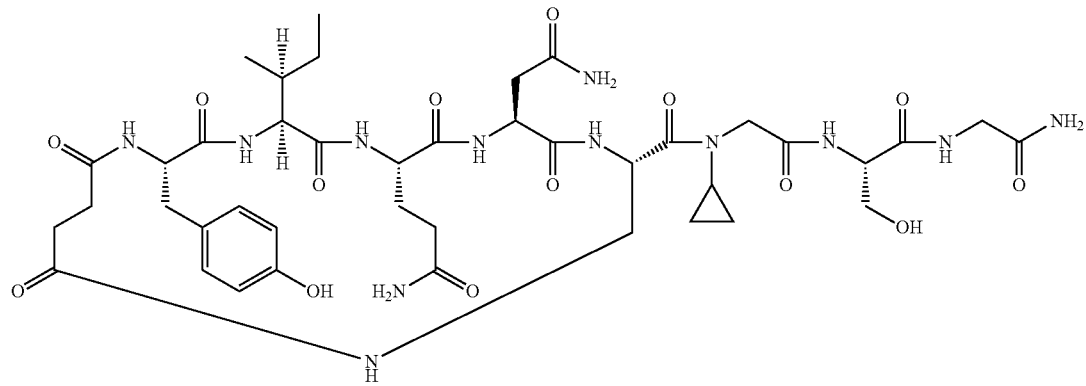 [SMILES: CC[C@H](C)[C@@H]1NC(=O)[C@H](Cc2ccc(O)cc2)NC(=O)CCC(=O)NC[C@@H](C(=O)N(CC(=O)N[C@@H](CO)C(=O)NCC(N)=O)C2CC2)NC(=O)[C@H](CC(N)=O)NC(=O)[C@H](CCC(N)=O)NC1=O]

The following amino acids were used: Fmoc-Gly-OH, Fmoc-Ser(tBu)-OH, Fmoc-CyclopropGly-OH, Fmoc-Dap(Boc)-OH, Fmoc-Asn(Trt)-OH, Fmoc-Gln(Trt)-OH, Fmoc-Ile-OH, Fmoc-Tyr(tBu)-OH and mono-tBu succinate.

MS (M+H$^+$): expected 945.0; observed 945.5

Material and Methods

Cell Culture and Stable Clone Production

Chines Hamster Ovary (CHO) cells were transfected with expression plasmids encoding either the human V1a, the human Oxytocin (OTR) or the human V2 receptor, the later in combination with the chimeric Gqs5 G protein to redirect the signal to Calcium flux. Stable cells were cloned by limiting dilution to yield monoclonal cell lines expressing either human V1a, human V2+Gqs5 or human OTR receptors and selected based on functional responses detected on a fluorometric imaging plate reader (FLIPR) detecting Calcium flux in the cell after receptor activation. The stable cell lines were grown in F-12 K Nutrient Mixture (Kaighns Modification), containing 10% foetal bovine serum (FBS), 1% penicillin-streptomycin, 1% L-glutamate, 200 ug/ml Geneticin at 37° C. in a 10% $CO_2$ incubator at 95% humidity.

Calcium Flux Assays Using Fluorescent Imaging (Fluorometric Imaging Plate Reader, FLIPR)

On the afternoon before the assay, cells were plated at a density of 50,000 cells/well into black 96 well plates with clear bottoms to allow cell inspection and fluorescence measurements from the bottom of each well. The density of cells was sufficient to yield a confluent monolayer the next day. Hanks balanced salt solution, without phenol red, containing 20 mM HEPES (pH 7.3) and 2.5 mM probenecid (assay buffer) was prepared fresh for each experiment. Compound dilutions were made using a Beckman Biomek 2000 laboratory automation workstation, in assay buffer containing 1% DMSO. The dye-loading buffer consisted of a final concentration of 2 µM Fluo-4-AM (dissolved in DMSO and pluronic acid) in assay buffer. The existing culture media was removed from the wells and 100 µl of the dye-loading buffer was added to each well and incubated for approximately 60 min at 37° C. in a 5% $CO_2$ incubator at 95% humidity. Once dye-loaded, the cells were washed thoroughly on an Embla cell washer with the assay buffer to remove any unincorporated dye. Exactly 100 µl assay buffer was left in each well.

Each 96 well plate containing dye-loaded cells was placed into the FLIPR machine and the laser intensity set to a suitable level to detect low basal fluorescence. To test compounds as agonists, 25 µl diluted compound was added to the plate 10 seconds into the fluorescent measurements and fluorescent response was recorded for 5 minutes. The fluorescence data was normalized to the endogenous full agonist dose-response set at 100% for the maximum response and 0% for the minimum. Each agonist concentration-response curve was constructed using a four parameter logistic equation with Microsoft Excel XLFit as follows: $Y = Minimum + ((Maximum - Minimum)/(1+10^{(LogEC50-X)nH}))$, where y is the % normalized fluorescence, minimum is the minimum y, maximum is the maximum y, $logEC_{50}$ is the $log_{10}$ concentration which produces 50% of the maximum induced fluorescence, x is the $log_{10}$ of the concentration of the agonist compound and H is the slope of the curve (the Hill Coefficient). The maximum value gives the efficacy of the agonist test compound in percentage. The concentration of agonist that produced a half-maximal response is represented by the $EC_{50}$ value, the logarithm of which yielded the $pEC_{50}$ value.

The following $EC_{50}$ (nM), and efficacy (%) for the specific peptides may be provided, together with comparative data for hV1a and hV2:

| Expl. | hOT $EC_{50}$(nM)/ efficacy (%) | hV1a $EC_{50}$ (nM) | hV2 $EC_{50}$ (nM)/ efficacy (%) |
|---|---|---|---|
| 1 | 1/105 | 5125 | 216/130 |
| 2 | 4/144 | >27000 | — |
| 3 | 0.9/113 | >27000 | 612/130 |
| 4 | 5/126 | — | — |
| 5 | 0.7/111 | >27000 | 1126/123 |
| 6 | 1/119 | >27000 | 364/104 |
| 7 | 3/101 | — | — |
| 8 | 1/134 | — | — |
| 9 | 1/132 | — | — |
| 10 | 1/130 | — | — |
| 11 | 3/128 | — | — |
| 12 | 1.6/130 | — | — |
| 13 | 8/128 | — | — |
| 14 | 6/122 | — | — |
| 15 | 8/123 | — | — |
| 16 | 4/100 | — | — |
| 17 | 0.6/114 | 351 | 116/116 |
| 18 | 2/130 | — | — |
| 19 | 0.4/114 | 470 | 59/114 |
| 20 | 0.9/117 | 562 | 174/112 |
| 21 | 4/126 | — | — |
| 22 | 0.8/109 | 391 | 176/106 |
| 23 | 3/123 | — | — |
| 24 | 0.5/104 | >27000 | 152/120 |
| 25 | 0.8/103 | >27000 | 213/118 |
| 26 | 0.5/107 | >27000 | 281/119 |
| 27 | 0.8/107 | >27000 | 282/114 |
| 28 | 0.5/109 | >27000 | 1385/119 |
| 29 | 0.6/109 | >27000 | 2068/113 |
| 30 | 2/109 | — | — |
| 31 | 0.5/107 | >27000 | 199/126 |
| 32 | 5/112 | — | — |
| 33 | 3/111 | — | — |
| 34 | 3/106 | — | — |
| 35 | 4/111 | — | — |
| 36 | 2/111 | — | — |
| 37 | 0.2/112 | >27000 | 53/121 |
| 38 | 0.38/126 | >27000 | 626/146 |
| 39 | 1.3/108 | — | — |
| 40 | 0.6/106 | — | — |
| 41 | 2.5/108 | — | — |
| 42 | 0.37/115 | — | — |
| 43 | 0.26/110 | — | — |
| 44 | 0.9/115 | — | — |
| 45 | 0.8/117 | — | — |

The compounds of formula I and the pharmaceutically acceptable salts of the compounds of formula I can be used as medicaments, e.g. in the form of pharmaceutical preparations. The pharmaceutical preparations can be administered preferably transdermal, intranasal, subcutaneous or intra venous (iv).

Transdermal is a route of administration wherein active ingredients are delivered across the skin for systematic distribution. Examples include transdermal patches used for medicine delivery, and transdermal implants used for medical or aesthetic purposes.

Nasal administration can be used to deliver drugs for either local or systemic effects, nasal sprays for local effect are quite common. Peptide drugs may be administered as nasal sprays to avoid drug degradation after oral administration.

Subcutaneous injections are also common for the administration of peptide drugs. An intramuscular injection is the injection of a substance directly into the muscle. It is one of several alternative methods for the administration of medications. It is often used for particular forms of medication that are administered in small amounts. The injections should be given under the skin.

The intravenous route is the infusion of liquid substances directly into a vein. Compared with other routes of administration, the intravenous route is the fastest way to deliver fluids and medications throughout the body.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of autism, stress, including post traumatic stress disorder, anxiety, including anxiety disorders and depression, schizophrenia, psychiatric disorders and memory, loss alcohol withdrawal, drug addiction and for the treatment of Prader-Willi Syndrome.

The dosage can vary within wide limits and will, of course, have to be adjusted to the individual requirements in each particular case. The dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be indicated.

The invention claimed is:

1. A compound of formula

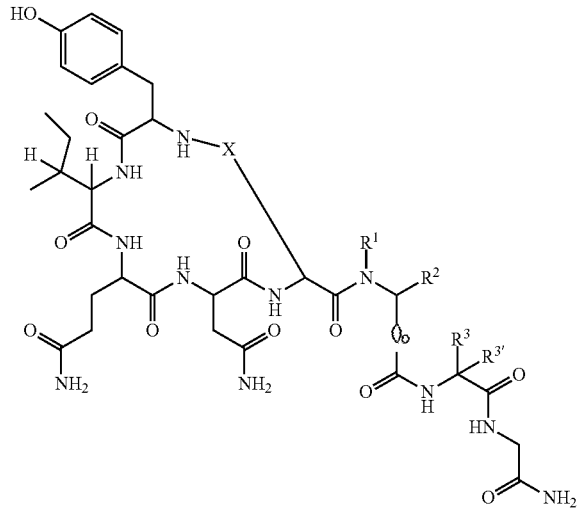

I wherein
$R^1$ is methyl or cyclopropyl;
$R^2$ is hydrogen;
$R^3$ is hydrogen, lower alkyl, lower alkyl substituted by hydroxy, —$(CH_2)_2C(O)NH_2$, benzyl, phenyl, —$CH_2$-five membered aromatic heterocyclic group, $CH_2$-indolyl, —$CH_2$-cycloalkyl, cycloalkyl or —$(CH_2)_2$—S-lower alkyl;
$R^{3'}$ is hydrogen or lower alkyl; or
X is —C(O)—$CHR^4$—$CHR^{4'}$—C(O)—NH—$CH_2$—
$R^4/R^{4'}$ are hydrogen or one of $R^4$ or $R^{4'}$ is amino:
o is 0 or 1;
or a pharmaceutically acceptable acid addition salt, a racemic mixture or its corresponding enantiomer and/or optical isomers thereof.

2. A compound of formula I according to claim 1, wherein o is 0.

3. A compound of formula I according to claim 1, selected from the group consisting of

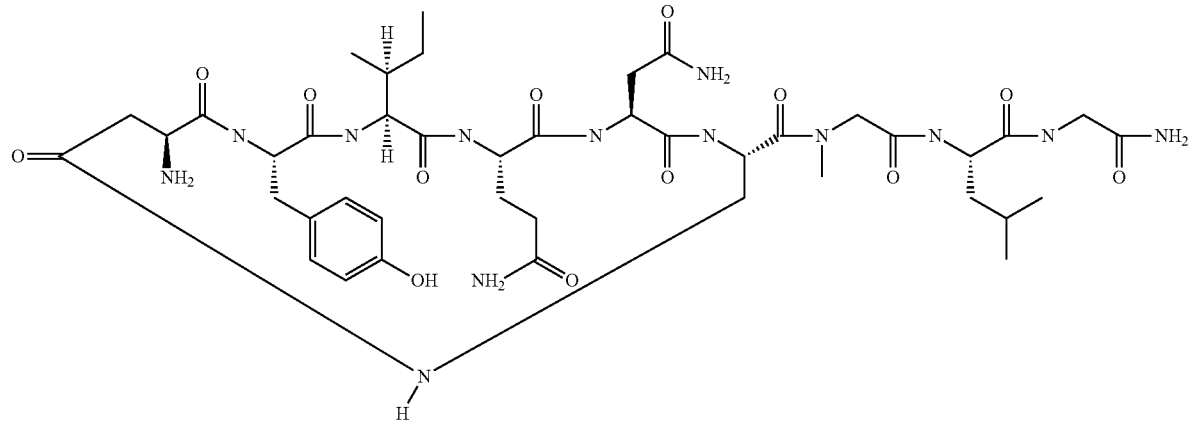

-continued
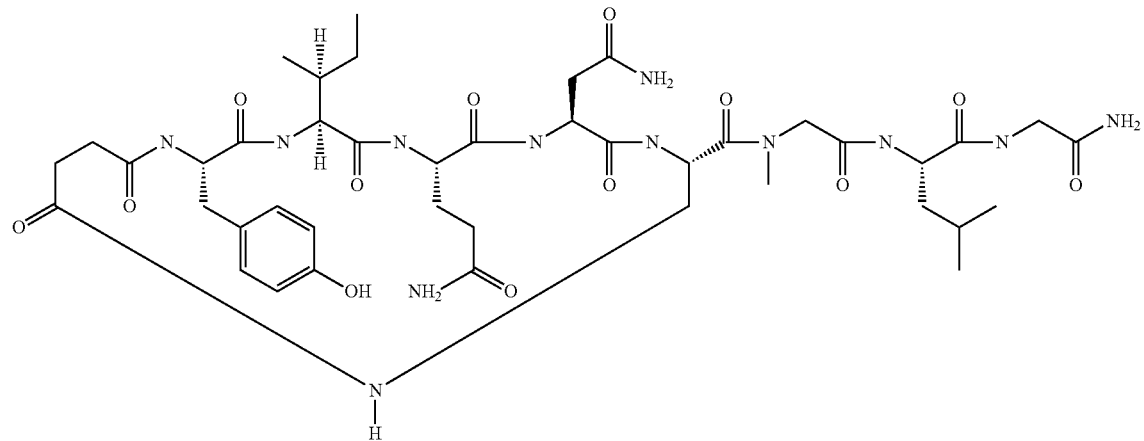
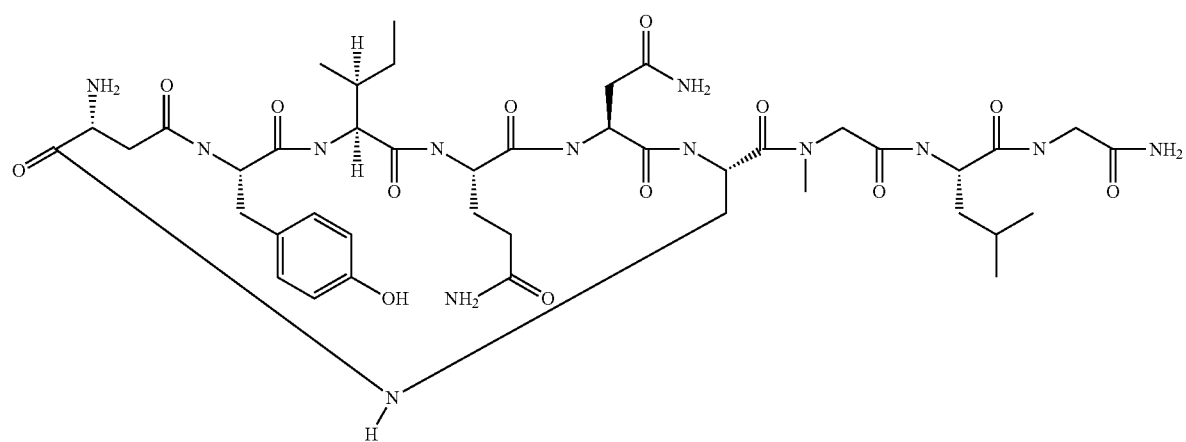
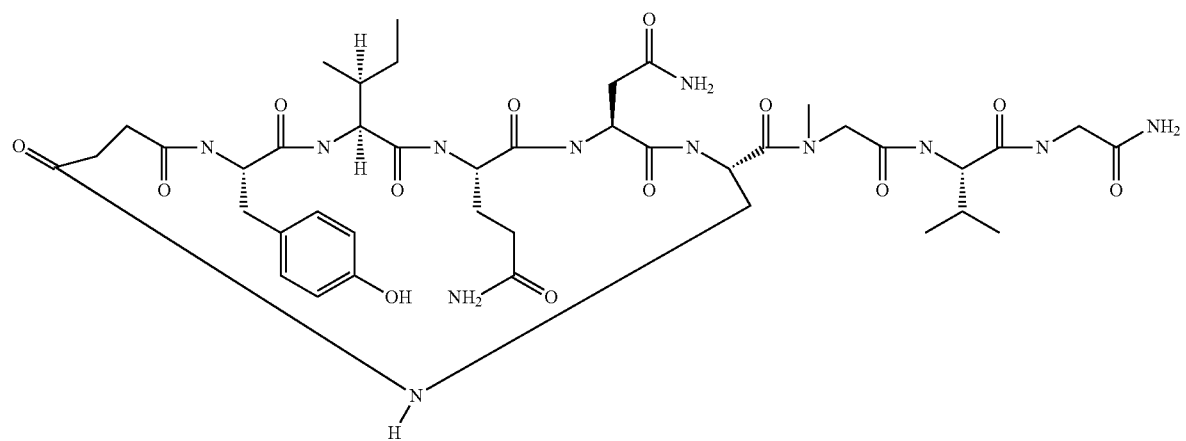

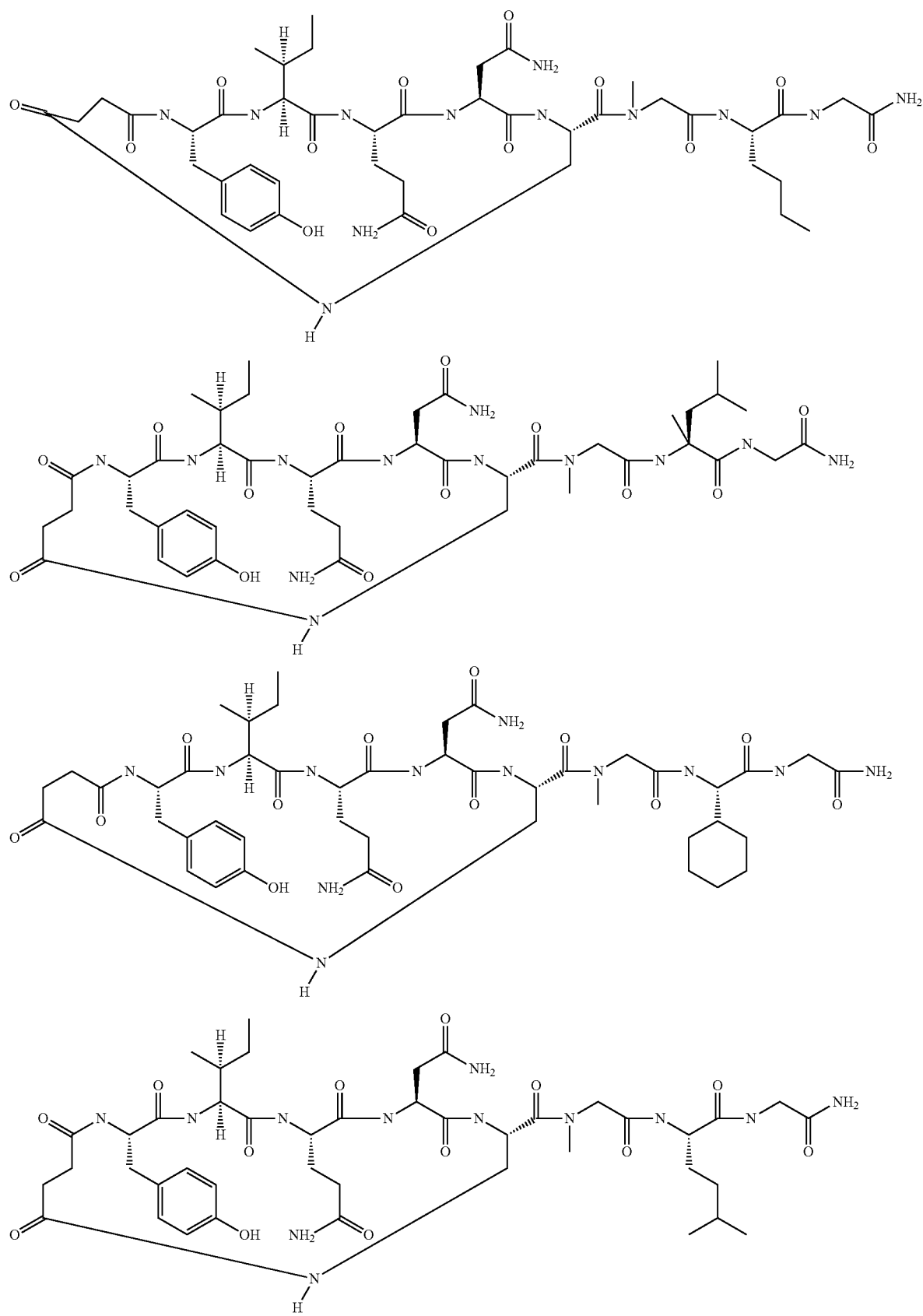

-continued
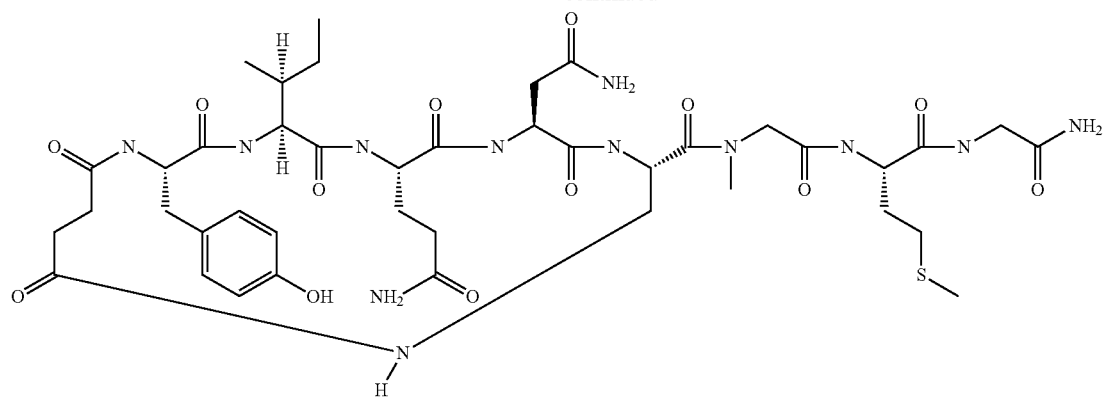
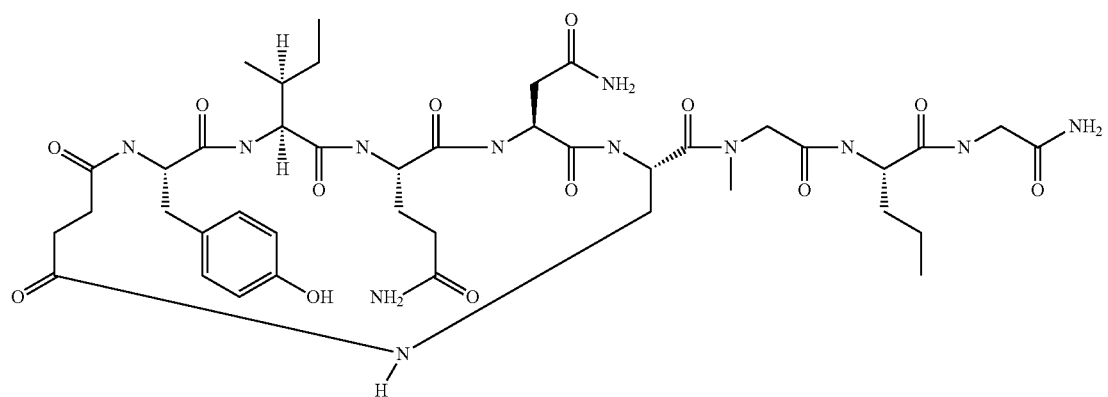
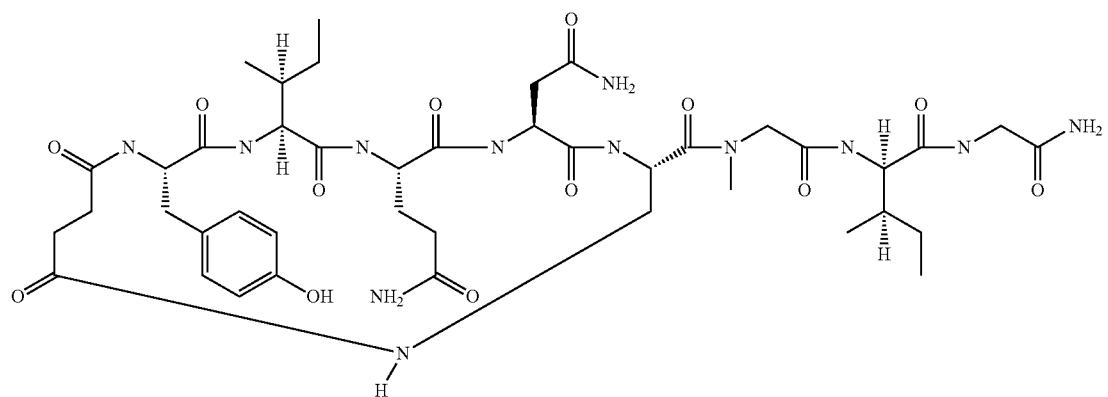
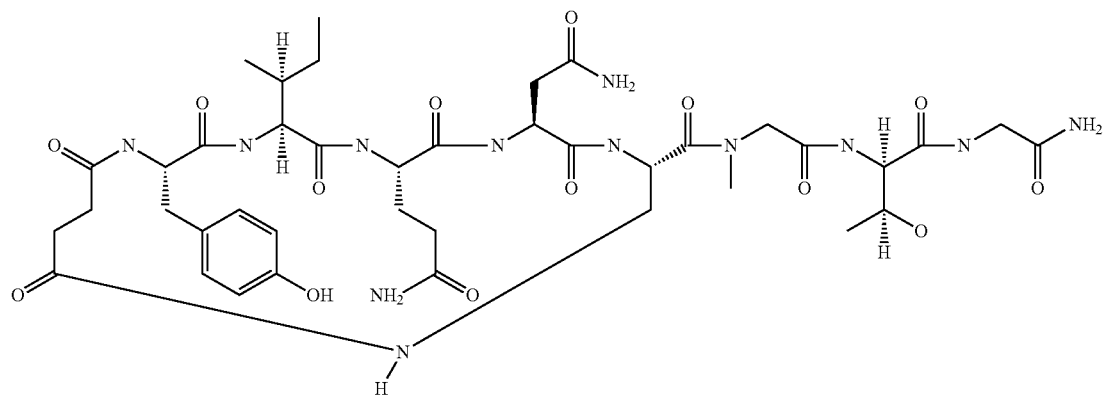

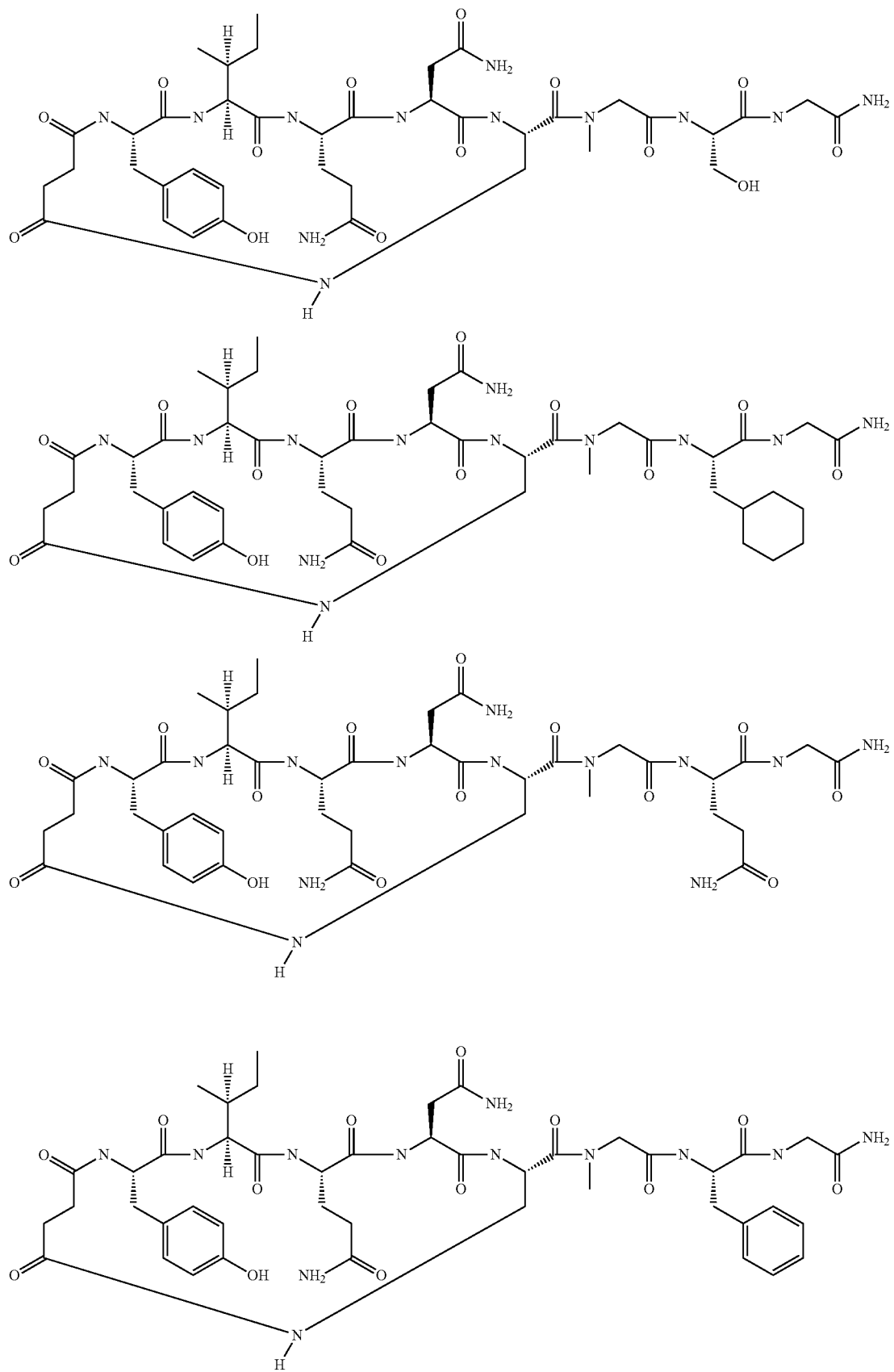

-continued
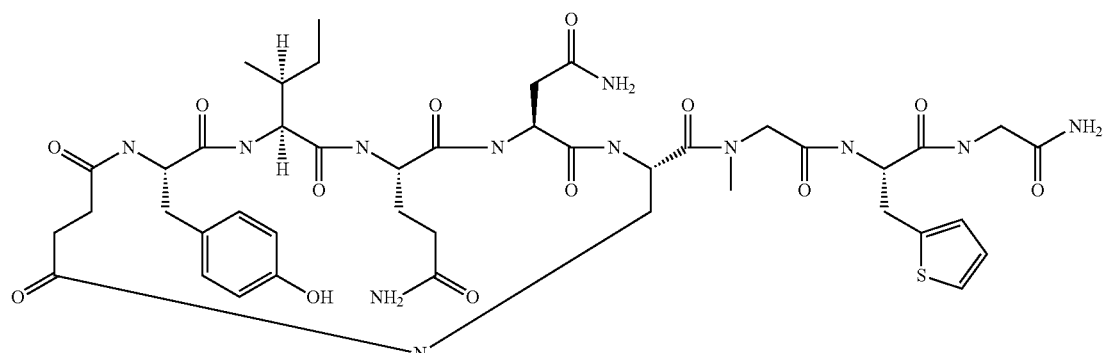
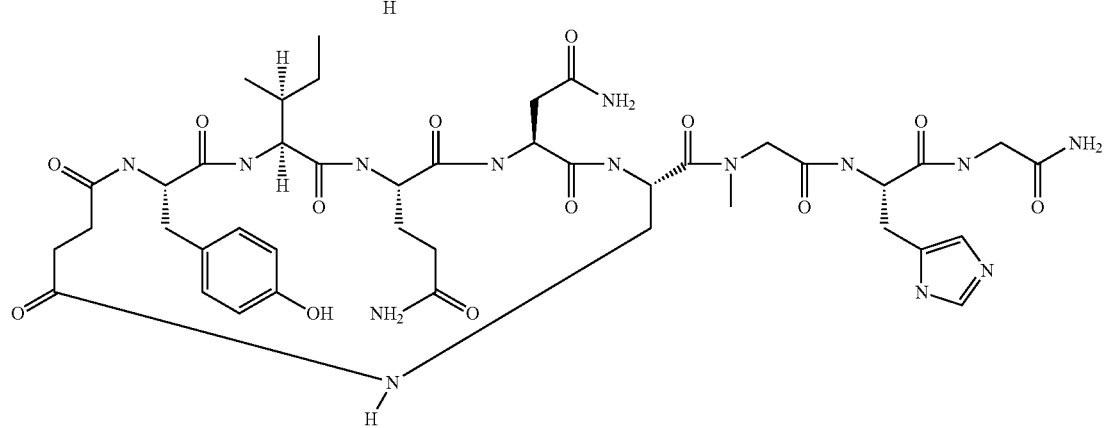
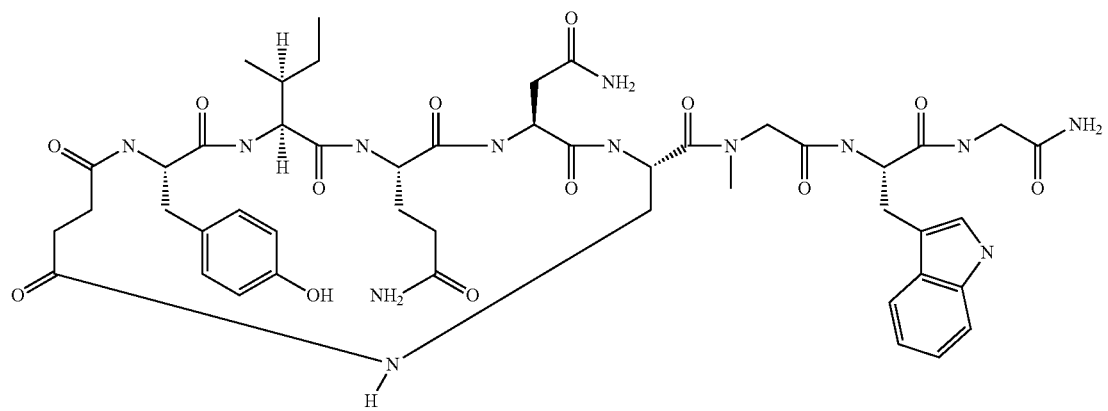
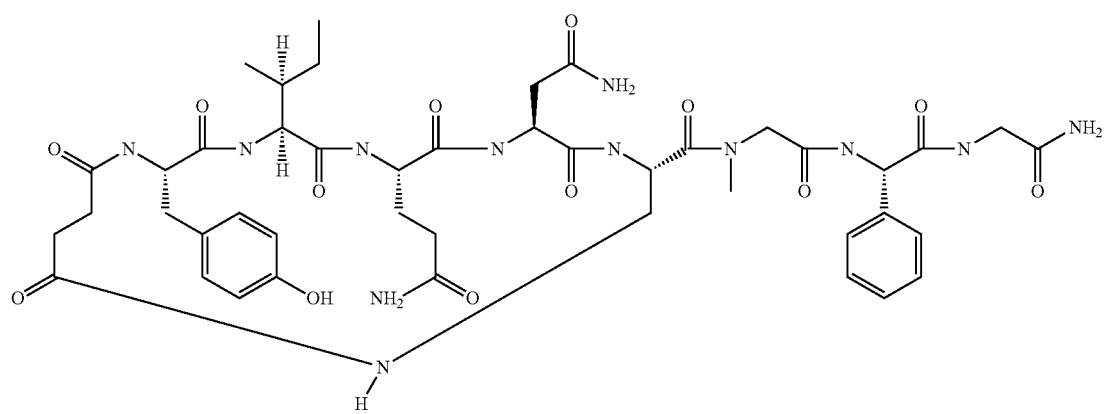

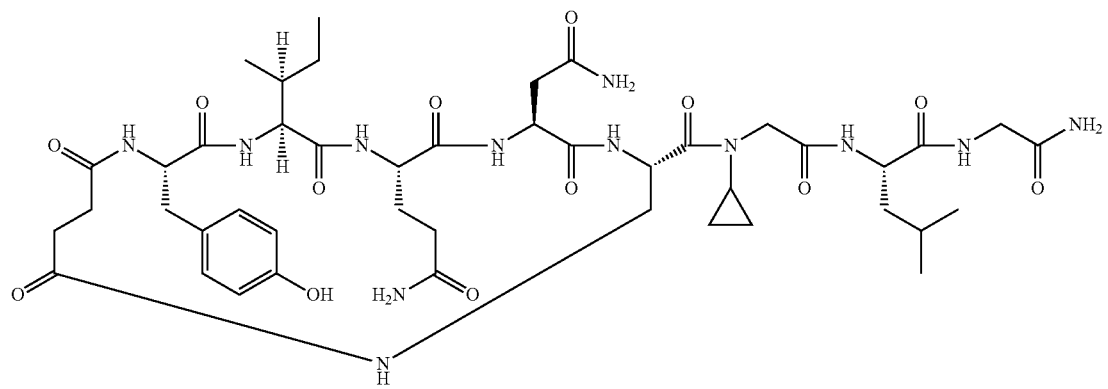
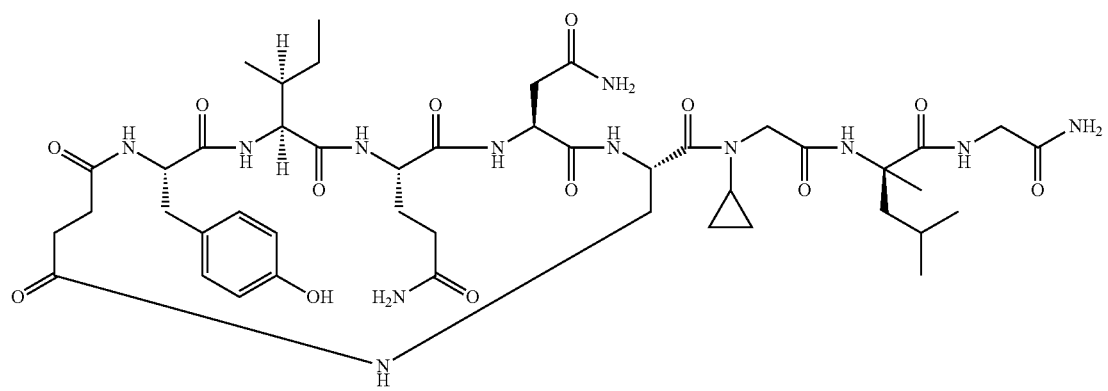
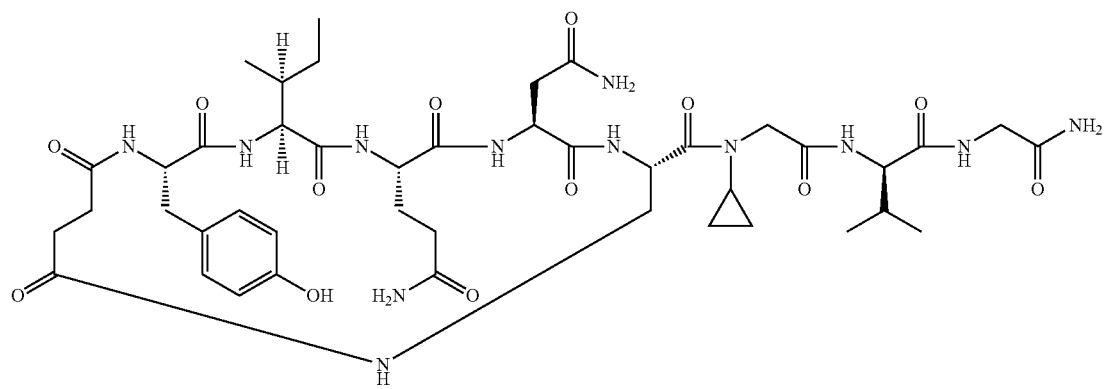
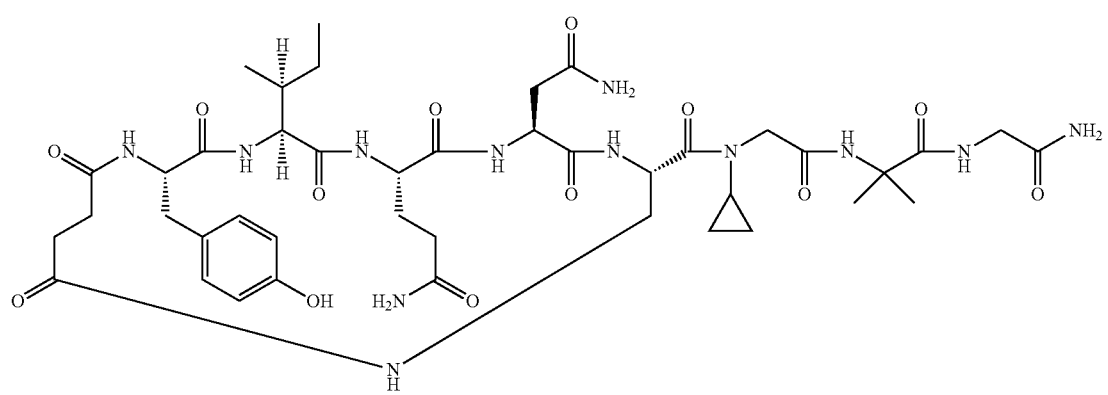

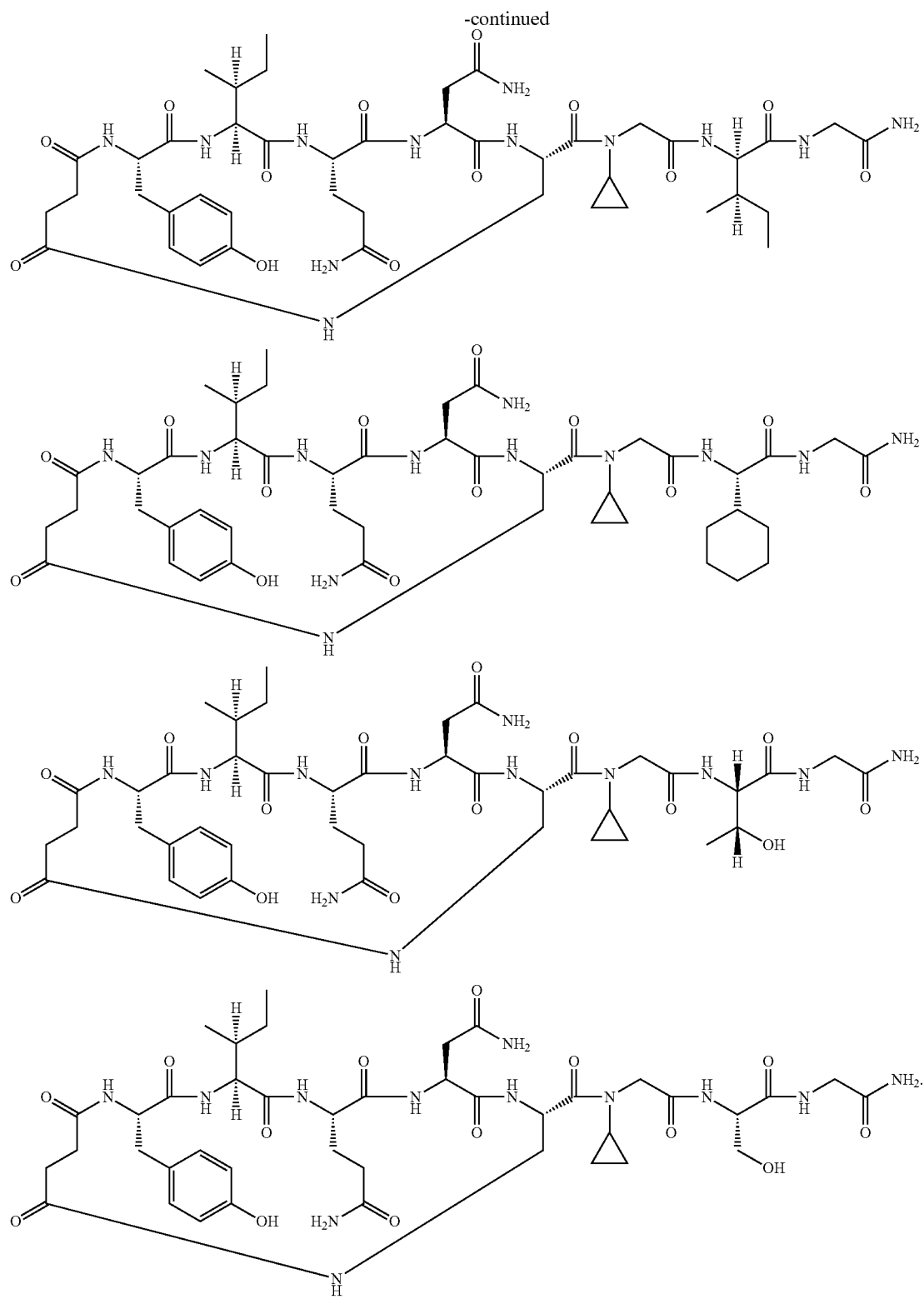

4. A pharmaceutical composition comprising a compound of formula I according to claim 1, and a pharmaceutical acceptable carrier and/or adjuvant.

5. A method of inhibiting the oxytocin receptor in a cell, comprising administering to the cell a compound of formula I according to claim 1.

6. A method of treating a disorder selected from autism, stress, an anxiety disorder, depression, schizophrenia, a psychiatric disorder, memory loss, alcohol withdrawal, drug addiction, or Prader-Willi Syndrome, comprising administering to a subject in need thereof a compound of formula I according to claim 1.

7. The method of claim 6, wherein the disorder is stress or an anxiety disorder.

8. The method of claim 7, wherein the disorder is post-traumatic stress disorder or anxiety.

\* \* \* \* \*